US006627745B1

(12) United States Patent
Kastner et al.

(10) Patent No.: US 6,627,745 B1
(45) Date of Patent: Sep. 30, 2003

(54) PYRIN GENE AND MUTANTS THEREOF, WHICH CAUSE FAMILIAL MEDITERRANEAN FEVER

(75) Inventors: Daniel L. Kastner, Bethesda, MD (US); Ivona Aksentijevichh, Bethesda, MD (US); Michael Centola, Tacoma Park, MD (US); Zuoming Deng, Gaithersburg, MD (US); Ramen Sood, Rockville, MD (US); Francis S. Collins, Rockville, MD (US); Trevor Blake, Laytonsville, MD (US); P. Paul Liu, Ellicott City, MD (US); Nathan Fischel-Ghodsian, Los Angeles, CA (US); Deborah L. Gumucio, Ann Arbor, MI (US); Robert I. Richards, North Adelaide (AU); Darrell O. Ricke, San Diego, CA (US); Norman A. Doggett, Santa Cruz, NM (US); Mordechai Pras, Tel-Hashomer (IL)

(73) Assignees: The United States of America as represented by the Department of Health and Human Services, Washington, DC (US); Cedars-Sinai Medical Center, Los Angeles, CA (US); University of California, Oakland, CA (US); University of Michigan, Ann Arbor, MI (US); Women's and Children's Hospital, North Adelaide (AU); Heller Institute for Medical Research, Tel-Hashomer (IL)

( * ) Notice: Subject to any disclaimer, the term of this patent is extended or adjusted under 35 U.S.C. 154(b) by 0 days.

(21) Appl. No.: 09/486,147
(22) PCT Filed: Aug. 20, 1998
(86) PCT No.: PCT/US98/17255
§ 371 (c)(1),
(2), (4) Date: Aug. 7, 2000
(87) PCT Pub. No.: WO99/09169
PCT Pub. Date: Feb. 25, 1999

Related U.S. Application Data

(60) Provisional application No. 60/056,217, filed on Aug. 21, 1997.

(51) Int. Cl.[7] .......................... C07H 21/04; C12Q 1/68
(52) U.S. Cl. ........................ 536/23.1; 536/24.3; 435/6; 435/91.2
(58) Field of Search ............................ 536/23.1, 24.33, 536/24.31, 24.3; 435/6, 91.2

(56) References Cited

U.S. PATENT DOCUMENTS 5,474,796 A * 12/1995 Brennan ..................... 427/2.13
5,840,686 A * 11/1998 Chader et al. ................ 514/12

FOREIGN PATENT DOCUMENTS

WO    Wo-95/17205    *  6/1995  ........... A61K/38/17

OTHER PUBLICATIONS

Telatar et al. "Molecular Genetic Testing for Familial Mediterranean Fever" Molecular Genetics and Metabolism. Vol 71, pp. 256–260, Oct. 2000.*
Pras et al. "Familial Mediterranean Fever: From the Clinical Syndrome to the cloning of the pyrin gene". Scand J. Rheumatol. VOl 27, pp. 92–97, 1998.*
New England Biolabs Catalog 96/97, p. 111.*
Boehringer Mannheim 1997 Bhochemical Catalog, p. 95.*
Ahren, "Biochemical Reagent Kits Offer Scientists good retun on investment" The Scientist, VOl 9, No. 1'5, p. 20, Jul. 24, 1995.*
Bernot et al. "Non–founder mutations in the MEFV gene establish this gene as the cause of familial Mediterranean fever (FMF)" *Human Molecular Genetics* 7(8):1317–25, Aug. 1998.
Bernot et al. "A transcriptional map of the FMF region" *Genomics* 50:147–160, 1998.
French FMF Consortium: "A candidate gene for familial Mediterranean fever" *Nature Genetics* 17(1):25–31, Sep. 1, 1997.
The International FMF Consortium: "Ancient Missense Mutations in a New Member of The RoRet Gene Family are Likely to Cause Familial Mediterranean Fever" *Cell* 90(4):797–807, Aug. 22, 1997.
Sood et al. "Construction of a 1–MB Restriction–Mapped Cosmid Contig Containing the Candidate Region for the Familial Mediterranean Fever Locus (MEFV)on Chromosome 16P13.3" 42(1):83–95, May 15, 1997.
McKusick et al. "Mediterranean fever, familial; MEFV" NCBI—Online XP–002090817, 1999.

* cited by examiner

*Primary Examiner*—Gary Benzion
*Assistant Examiner*—Jeanine Goldberg
(74) *Attorney, Agent, or Firm*—Needle & Rosenberg, P.C.

(57) ABSTRACT

The invention provides the nucleic acid sequence encoding the protein associated with familial Mediterranean fever (FMF). The cDNA sequence is designated as MEFV. The invention is also directed towards fragments of the DNA sequence, as well as the corresponding sequence for the RNA transcript and fragments thereof. Another aspect of the invention provides the amino acid sequence for a protein (pyrin) associated with FMF. The invention is directed towards both the full length amino acid sequence, fusion proteins containing the amino acid sequence and fragments thereof. The invention is also directed towards mutants of the nucleic acid and amino acid sequences associated with FMF. In particular, the invention discloses three missense mutations, clustered in within about 40 to 50 amino acids, in the highly conserved rfp (B30.2) domain at the C-terminal of the protein. These mutants include M6801, M694V, K695R, and V726A. Additionally, the invention includes methods for diagnosing a patient at risk for having FMF and kits therefor.

3 Claims, 14 Drawing Sheets

FIG. 1

```
1     TATTTTTGTA TTTTAGTAGA GATGGGGTTT ACTGTGTTGG CCAGGCTGGT CTTGTACTCC
61    CAACCTGAGG TGATCCACCC ACCTCGGCCT CCCAAAGTGC TGGGATTACA GGCGTTAGCA
121   CTGTGCCCTG CCCCCAACAT GTAACTTCTG TTAGCTTCAA AGCCACCTCT GGGGCCCTGC
181   ACCACATATG AGCTGAAGGA CACCCGTGCC TTTTCACCCG TGTAGCTCCA GCATCTTGGC
241   ACACTGTCTA GAATGTTCAA TGAATGTGCA CGGAAGAGCA TTCTGGCTCC AGGGAGCGAG
301   GACTGAGTCA GCTCTGGGAA CAGATGAGTC AGGCTGGTGG TCCAGGCATT GCTTTTCAAG
361   TCCTTCATGT GGCTGGAAGA ACCAGTCAAC TGAACCCGA TCAACAGGGG TGATGGCATG
421   GCAAGAGTTA TCTCCTGGCA GTGCCCTTCT GGCCTCACTT GCCTTCTTGG GCCAGGAAAG
481   GCAAAGCTCA CAGGACTGTA TTCAGTGCCC ACCCCTTCCC CCGTCCTGTG CCATTGGCTC
541   TGGAAGGTCC CTGAAACCCC GAGTCTGGAG GAGAACAGTT GACCAGCAGG GCGGGCCCTC
601   AGCATAGTCC TCTCTGTTCC CACTCACCCG CTCTGCCAGC CCCAGATCCT GGCAGGAAGG
661   AAGATTGGAG GGGGTGTCTG GAATCCAATC CCAGACCTTC CCTTGCAGAC TTGCCCATCT
721   GTCTGTGGTC TAGTGTGGAG GCGAGGTCCA GGGTTTGGGA GGGGTGTGGG GGCACATGTC
781   TGCCAAGGCA TGGAGCCCTC CCAGCTGGAA AATCCTCTGA ACCTGTAAGA AGAGAACACA
841   GCCGGCATGG ACACACCCTT ACCCTTAGTC TCAGTTCCCA CCAAGACACA GAGCATTTCC
901   TGTGCCTTTT CCGCTATTTC ACAACCTGCC TTTTCTTGCT CACCAAGGAC AGAGGCTTCT
961   TTTCCTACCA GAAGCCAGAC AGCTGGCTCG AGCCTCTCCT GCTCAGCACC ATGGCTAAGA
1021  CCCTAGTGA CCATCTGCTG TCCACCCTGG AGGAGCTGGT GCCCTATGAC TTCGAGAAGT
1081  TCAAGTTCAA GCTGCAGAAC ACCAGTGTGC AGAAGGAGCA CTCCAGGATC CCCCGGAGCC
1141  AGATCCAGAG AGCCAGGCCG GTGAAGATGG CCACTCTGCT GGTCACCTAC TATGGGGAAG
1201  AGTACGCCGT GCAGCTCACC CTGCAGGTCC TGCGGGCCAT CAACCAGCGC CTGCTGGCCG
1261  AGGAGCTCCA CAGGGCAGCC ATTCAGGGTA AGCGGGCCCA GGCCTCCTCC TCATCCAGTG
1321  CTGAGTGCTG GCTGCTTTGT GGGAAGGGG ACCAGGAGCT CAGAGCAGCT CACTCTGACC
1381  TGGGGATTGG GAGTCTCAGG TCTACCAAAA TCCAGATGAC TTTAGTTCAG GAACGTCCCT
1441  TTCTTCACTC TGGCCTTTGG AACTGGGTTA GTAAACTTCC TTCAGGCTCC TAATGGTTTT
1501  TTTAAGAAGC AGGTCAGGGT CACGAAAGC AGGAGCTGGA ACACCTGTTC TTTGAGACTT
1561  CTTCACTACA TTTATGATTA ATACTCATGT CAGACAAACA TCTCTAGGTT AGCAAAAAGG
1621  GATTGCTATG CAATCATATG AACGGGGTTG GTATAGAATC TTCTCAGTGC TGTTCACCAT
1681  GTTGGCCAGG CTGGTCTCGA ACTCCTGACC TCAAGTGATC CTCCCGCCTC AGCCTCCCAA
1741  AGTGCTGGGA TTCAGACAT AGGCCACCGT GCCCGGCTTA TTTTTATTTT TAAAGCGTAT
1801  AATCTGGGTT TTGCTGACCT GTGTAAGATC TTATTTGAAA CAGTTGTCCT GCTTAAAACG
1861  TTTGAAAAGT ACTATTTGAG AAATATAGCC TAGGCATGGT GGCTCACACT TATAAATAAT
1921  CTCAGCACTT TGGGAGGCTA AGGTGGGTGG ATTGCTAGAG CTCAGGAGTT TGAGACCAGC
1981  TTGGGCAACA TGGTGAAACC CTGTCTCTAC CAAAAATACA AAAAATGAG CCAGGCGTGG
2041  TAGCACACAC CTGTATTTTC AGCTATTGAA AAAACAGAAA ACAGGCTGAG GTGAGAGGAT
2101  TGCTTGAGCC TGGGAGGCAG AGGTTGCAGT GAGCTGAGAT CACATCAGGG CAACAGAGCA
2161  AGATCCTGTC TCAAAAAATA AAATAAGAGA GAGAGAAATA CATAGCAACA TCAAGCATGT
2221  TCTTACTGAA TGGTAATTGA CTGCCATTGT CTAGTCTGGG NAGTCCTGAA CTTTTGTTTT
2281  TGAGATGGAG TCTTGCTCTG TCACTCAGGC TGGAGTGCAG TGGCCCGATC TCAGCTCNCT
2341  GCAACCTCCA CATCCCGGGC TCAAGCGATT CTCATGCCTC AGCCTCCCGA GTAGCTGGGA
```

FIG. 1 (CONT.)

```
2401 CTACAGGTGC GCACCACCGC GTCTGGCTGA GTTTCTTATT TTTAGTAGGA ACGGGGTTTT
2461 GCCATGTTGG CCAGGCTGGT CTCGAACTCC TGACCTCAAA TGATCCTCCC ACCTTGGCCT
2521 CTGGAGAAGC TGGGATTACA GGCATGCGCA CCACGCTCAG CTTATTTTG TATTTTTAGT
2581 AGAGACGGGG TTTCACCCTG TTGGTCTTGA ACTCCTGATC TCAGGTGATC CTCCCGCCTC
2641 GGCCTCCCAG AGTGCCGGGA ATACAGGCAT GAGCCACCGC GCCCGGCCCG TTGTTTTCCT
2701 CAATTTCTAA ACTTTAATAT CCAAGGGAT TCTCTCTCCT CTGCCCTGAA TCTTGGGCCC
2761 TAAACGTGGG ACAGCTTCAT CATTTTGCAT CTGGTTGTCC TTCCAGAATA TTCCACACAA
2821 GAAAACGGCA CAGATGATTC CGCAGCGTCC AGCTCCCTGG GGAGAACAA GCCCAGGAGC
2881 CTGAAGACTC CAGACCACCC CGAGGGAAC GAGGGGAACG GCCCTCGGCC GTACGGGGC
2941 GGAGCTGCCA GCCTGCGGTG CAGCCAGCCC GAGGCCGGA GGGGCTGTC GAGGAAGCCC
3001 CTGAGCAAAC GCAGAGAA GGCCTCGGAG GGCCTGGACG CGCAGGGCAA GCCTCGGACC
3061 CGGAGCCCGG CCCTGCCGGG CGGGAGAAGC CCCGGCCCCT GCAGGGCGCT AGAGGGGGGC
3121 CAGGCCGAGG TCCGCTGCG CAGAAACGCC AGCTCCGCGG GGAGGCTGCA GGGCTGGCG
3181 GGGGCGCCC CGGGCAGAA GGAGTGCAGG CCCTTCGAAG TGTACCTGCC CTCGGGAAAG
3241 ATGCGACCTA GAAGCCTTGA GGTCACCATT TCTACAGGGG AGAAGGCGCC CGCAAATCCA
3301 GAAATTCTCC TGACTCTAGA GGAAAAGACA GCTGCGAATC TGGACTCGGC AACAGAACCC
3361 CGGGCAAGGC CCACTCCGGA TGGAGGGCA TCTGCGGACC TGAAGGAAGG CCCTGGAAAT
3421 CCAGAACATT CGGTCACCGG TAAATTGTGT TCTTTCCAAC TTTATATCGG CTGCAGAGAA
3481 AGAATGGCTG GCCGGGCACG ATAGCTCATG CCTGTAATCC CAGCGCTTTG GGAGGCCAGG
3541 GCGGGAGGAT TGCTGGAGGC CAAGACTTTG AGACCAGCCT GGTGAATGTA GTGAGACCCC
3601 CGCCATCTCT ATAAACGAAA TTAAAAAAAT AAAAACCCAA AGGTTGGCA GGGCGTGGTA
3661 GCTCTCGCCT GTAATCCCAG AGCTTGAGA GGCTGCACG GAGGATCTC TTGACCCCAG
3721 GAGTTCCATA CTAGCCTAGG CAACACAGTG AGACCCATC TCTACAAAAT ACAATAGTGG
3781 CACGCGCCTG TAGTCCCAGC TGCTCGGGTT CACTTGAGCA GACGGAGTTC CAGGCTACAG
3841 TGAGCTGAGG ATCATGCCAC TGCACACCAG CCTGAGCAAC GTAGCCAGAC TCACTTCTAC
3901 AAAACTAAAA AAAAAATTAG CTGGGTATGG TGGCACACGC CTGTAATTCT AGCCACTCAG
3961 GAAGCTGAGG CAGGAGGATT GCTTGAGCCA GGGAGTTCCA GGCTGCAGTG AGCTGAGGAT
4021 GTGCCACTGC ACTCCGGCCT GGGCAACAGA GCAAGACCCT GTCTCTTAAA CATTTTGGGG
4081 GGAAAAAAAA AGAAAGAAAG AATGTCCGAT TGAAAAAGGC AATCAGGTGT TATCAGTGGC
4141 CAAAGAATGG AGAAGGGAG CTCACCTCTG CAGGCGTCTG CTTGCCAGGG ATGGGAGGCA
4201 GGCGATTTT AGAGTCCAGG GAGGGAAGG GAGATAGGTA AGCAGGCCCA GGCAGGGTT
4261 CCATATGTGC AGGCGCTGTC CCCAGCATGC TTCTTCCTAC ATGGCATTCA AACAAACCCT
4321 TCTCCATCTT CTTTAGGGGA GGACCCTTTA GCTTATAACC ATGTGTAAAT GATCCTAAGG
4381 TAACTGGAAG TCACCTCTTC CAGTTTGCAC TGGTTTTGCT CTGATCTTAA CTTCCTCTGG
4441 TTTTTGGCAA GGGATCAGGA GGCTCCAGGC CATCTGGATT TTTTAAGCA GCTGTCCCTA
4501 TAGGTAAAGA GACTAAAAAA AAACTGTAAA AGAAAAATGC CACCAGTTTA GAGGGTACCG
4561 AGGCTATCCA GGTGACAATT CCATGCTCGT GGTGGGGCA GCATTCAGAA ACACACTTTC
4621 CTTTTTTC CTCCTTTTT TTTTGAGAC AGAGTCTCAG TCTGTCTCCC ATGCTGGAGT
4681 GCAGTAGTGT GAGCACAGTT TACTGCAGCC TCAACCTCCT AGGCTCAAGC GATCCTCCCA
4741 CCTCAGCCTT CCAAGTAGCT GAGACTATAG GTGCTCACCA CCACACCTGG TTAATTTTTT
```

FIG. 1 (CONT.)

```
4801 TTTTTTTTTT TGTATTTTTT GTAGTTACGA GGACTGTCTA TGTTGCCCAG GCTGGTTTTG
4861 AACTCTTGGG CTCAAGCGAT CCCCCGCCTT AGCCTCTAAA AGTGCTAGGA TTTCAGGTGT
4921 GAGTCACTAC ACCCAGCCTA TGAACACAC TTTCCAATGC ATTGTTGGCT GGAGAGGAGA
4981 AATCACAGCA CTCAAGGAGG AGAAATAGAA TTGGGGGTCC AGCCGGGTG CGGTGGCTCA
5041 TACCTGTAAT CCCAGCACTT TGGGAGGCCA ATGGGGCGG ATCACCTGAG GTGAGGAGTT
5101 CGAGACCAGC CTGCCAACAT GGTGAAACGC CATCTCTACT AAAAATACTA AATTTGCTGG
5161 GCGTGGTGGC GGGTGTCCAT AATCCCAGCT ACTCAGAAGG CTTCGAGGCA GGAGAATTGC
5221 TTGAACCGAG GAGGCAGAGG TTGCAGTGAG CCAAGATCAT GCCACTGCAC TCTAGCCTGG
5281 GCGACAAGAG CAAAACTCTG TCTCAAAAAA AAAAAAAAAA AGAATTGGG AGTCCAGGGA
5341 CCCCTGAGAC CTGGGAGGGG AAAGGATGTG GTATGCTGCA TGAGTCTTCA AATCCAGAAG
5401 TCCCTGGGTC TTCCAGTGAG AAAGGACCCT GGGATCTGGA AAACCTAGCA TCCTTAGGAA
5461 TAGTGACCTG AAAAGTACTG AAGTATTTCC CCCCTAATTT TCTTTTATCC CTACTGTATT
5521 TTTTTTAATT TTTTTTTTTT TTTAGATATG GGGTCTTGCT ATGTTGCCCA GGTTGGTCTC
5581 GAACTCCTGA TCTCAAACAA TCCTCCCATC TTTGCCTCCG AAACTGCTGG GATTACAGGT
5641 GTGCACCACT GCACCAGGTC CCCACTGTAT TTATATCATT GGGATTCCTG GGTGTCTTCT
5701 AGGGCCGCTT CGTTAATCTG ATGCAGGCTT AGACCCTGAA AAATGCATAT ATGCACAGCT
5761 TCACAAATGT CACATCAAAT TTCAGGTAGT TCTTGGACAC TCTGAAGACC ATCTTTAGAA
5821 TCCAAGGGGT TTATGGACAC CAGGTAGAAA ATCTGGGAA GACTGGTTAA AAATACTCCC
5881 TCTCACAATA ACCTCACAGC AATGCATCAT CATGGGGTTG AGATTCTACC ATTGCCTTTC
5941 TCTCAGCAGA AGAAAAGCC TATTGGCTAA AGTCCTAACT ATCTACTGCT GAGGTAGTCA
6001 TTAAAATTAT GTTTGGTTGT GAATAATAGA AACACCCAAA TAACAGTAAC CTCAACAGAA
6061 AAGAAGTTTG TGCCTCCTTC ACATAAATGA TACACAGGCG GTCCAGGCA GATCCGTGGG
6121 CCAGGACCCT GGGTCCTGC TGTTGCTCTG TCCACCAAG TTTGTCCTCA AGCTTCTGCT
6181 CTCAGAAGGT GACGTCCTCA TGCCAGGCAG CAAGATGGAG GAACAGAGGG GAACAGTATC
6241 CCTCGGGAAA GCTCTAGAAG TTTCTAGAAG CTGCTTGTGA CACCTCCATT TACATCCCTT
6301 TGGTCATATT ATTGTCAAAT AGCCACACCT AACTGCAAAG GAGGCTGAGA AATGCAGGGC
6361 ATTTGGGGGG CAATGGGAGG CAGGGAAACA GGGAAACGTG ACAATTAAT TCTATCACGA
6421 GAGAAGGAGG GAGAGTAATT TCTGGTGACT ACTAGCAGTC TCATTTACAG ATGTGCTGTG
6481 AATTCTGGG ACACTGTGAG GTGGGAGGAG GTAGCAGGGG CTAAAGGATT GAGTGTGTTT
6541 CTATTTCTTT TTTTGTTTTT TTTTTTTTTG AGATGGAGTC TCTCTTGGTC ACCCAGACTG
6601 GAGTGCAGTG GCGCAACTTC AGCTCACTGC AAACTCCGCC TCCGGGTTC AAGCAATTCT
6661 CCTGCCTCAG CCTCCCGAGT AGCTGGGATT ACAGGTGCCC ACCACCACGT CCGGCTAATT
6721 TTTGTATTTT TAGTAGAGAC AGGGTTTCAC CATCTTGGCC AGGCTGGTCT TGAACTCCTG
6781 ACCTCATGAC CCACCCGCCT CGGCCTCCCA AAGTGCTGGG ATTACAGGCG TGAGCCACTG
6841 CGCTCGGCCT TGTGTTTCTA TTTCTTCTTG TATCTCGTGG CATGTCTGCT TATGAAGTTG
6901 CAATTAGAGT CTTGGAGTAG AGCTATTCAT AACTGTTAGG TCTTCATGAT GAGTTCCAGT
6961 CTTTAGCCCT ATAATGCCCC CCTTCTTTGC TTTTTCTTTT AAGATGGCAT CTTACTCTGT
7021 TGCCCAGGCT GGAGTGCAGT GGTGCAGCAT CAACCTCCTA GGTTCAAGCA ATCCTCCTGT
7081 CTCAGCCTCC CAAGTAGCTG GGATTAGAGG TGTGCACCAC CACACCTGGC TAATTTTTTA
7141 ATTTTTGTA GAGGTGGGCT CTTGCCATGT TGCCCAGGCT GGTCTCAAAC TCCTGAGCTT
```

FIG. I (CONT.)

```
7201  AAGCAGTCCT CCCACCTTGG CCTCCCAAAG CACTGGGATT ATAGGCATGA GCCACCACCC
7261  AGCCCCTTCT TTGCTTTCAT TTAATGGTTA TTGAACTCAT ATGTGAGCAG TGGTCTATTT
7321  ATTCCTTCAT TCAATACTCA TTTTCCAAAT GCTTGCATTT GCCAGGTACT CTGCTAGGGG
7381  CTGGGATCCA GCTAGGAGCG AGGTACACAA GTCACCATCC CCTGGAAGCC TCCACTCACG
7441  TTATGGGCAG CCAGGGATGG GTTCAAGTGG CAAAGGAACA CTGGTCAGAA TGTCTCTTTC
7501  CTTGGCATCA CCTGCTAGAT CTATGTCTGT GCAGGAGGAA CAGCACAAGG CCATGGGTCT
7561  TTCTTTAGGA TAAATGCCCA AGAATTCCAA GGCTCAGGAA TGTCTGAGGT CTGGCCCTTA
7621  GCTCTCAGGC CCAGTGGCCT GTTTGCTTCC TCACTGGATG GAAGTCGGGG GAGGACAAGC
7681  TAGGAAGTGG GCAGAGTCTA ACTGAGAACT CGCACATCTC AGGCAAGGGC TGTGTCCGCT
7741  GTGCTTTGTG ATACCTCTGT GTAAGCAACT TGGGTTTGCC ATTCAGGGGG TTTTTCCACT
7801  GCATGTCCCC AGGAAGGCCA CCAGACACGG CTGCGAGTCC CCGCTGCCAC GCCCAGGAAG
7861  GAGACCCAGT TGACGGTACC TGTGTGCGTG ATTCCTGCAG CTTCCCCGAG GCAGTTTCTG
7921  GGCACCCCA GGCCTCAGGC AGCCGCTCAC CTGGCTGCCC CCGGTGCCAG GACTCCCATG
7981  AAAGGAAGAG CCCGGGAAGC CTAAGCCCCC AGCCCCTGCC ACAGTGTAAG CGCCACCTGA
8041  AGCAGGTCCA GCTGCTCTTC TGTGAGGATC ACGATGAGCC CATCTGCCTC ATCTGCAGTC
8101  TGAGTCAGGA GCACCAAGGC CACCGGGTGC GCCCATGA GGAGGTCGCC CTGAACACA
8161  AGGTAGGCAC TCCCTGCCTG TGGGCTCTTC TCTGCCAGGC ACTTGGACAC ACTGGGCCTT
8221  ACTTCATTTT CCCAACAACT CTGGGTTGTT GGTGCATTAA CCAGCATTCT TGGGCTGGAA
8281  ATGGCAAGAA CACAATATAA ACCAGTCCAG CAAAGAGGGG AGCTACAGGT TTATGTTGCT
8341  CAGAGATCCA GGGGAGCTG GCTTCAGGTA TGGCTGAATC CAGAGGCTCA GAGGAAGTGC
8401  CTCTCAGCTC TGCTGCCTTT GGCAATTCAG CCATTCCTCC CTCCTCTTTC CTGAGCACCC
8461  CTCCCCATGC CGCTGGCAGC AGCACCCTCA GCCTTGCTAC CAGAAGGAGA TGTTCCCCTC
8521  CAGAGTTGGC ACCAGCTAAA GATGGCAGGA GCCAAATTCA AGCTTTTCAA CAAGTGCTGT
8581  TTTTCCAGAA GAAAATTCAG AAGCAGCTGG AGCATCTGAA GAAGCTGAGA AAATCAGGGG
8641  AGGAGCAGCG ATCCTATGGG GAGGAGAAGG CAGTGAGCTT TCTGGTAAGG TCAGAGGTGG
8701  CTGATGGCCC ATCCGTCCCT GGAGGAAGG TGGAAGAGT GAGCAGGGT CCCCGAGATT
8761  CTGCTGTGGT TCACAGGGCA GCAGGATGG CCACCTCCTC TCAGGGACA GAGGGTAACC
8821  AGCAGCCAAG GGTAAGCTCA TCCCTGTAGA GGGAGACCAC CCCCAGCAGG CAGGGGTCAC
8881  CTCTGAGGAT CCTGTCATGC TTTCTCATAC TCACCAGAAG ATGGTAGAGA GCAACCTATG
8941  CCGGTGACTA CTGCAGAAAG ATGGGATTGA GGAAAAGGGA GGAGAACGCC ACTTTCTTTT
9001  TTTGTGACGG AGTCTCGCTC TGTCACCCAG GTTGTAGTGC AGTGGTGTGA TCTTGGCTCA
9061  CTGCAACCTC TGCCTCCCGG GTTCAAGCGA TTCTCCTGCC TCAGCCTCCT GAGTAGCTGG
9121  GATTATAGGT GAGTGCCACC ATGCCTGGCT AATTTTTGTA GTTTAGTAG AGATGGGGTT
9181  TCACCATGTT GGTCAGGCTG TTCTCGAACT CCTGAACTCG TGATCCGCCC GCCTTGGCCT
9241  CCCAAAGTAC TGGGATTACA GATGTGAGCC ACTGCGCCCG GCCAAGAACA CTTTTAACTT
9301  CATAATTTAC TCTCTGTTTT TTGTTTTGT TTCCAAGATG GAGTCTCGCT CTGTCACCCA
9361  GGCTGGAGTA CAGTGGCACG ATCTTGGCTT GCTCCAACCT CCACCTCCGA GGTTCAAGCA
9421  ATTCTCCTGC CTCAGCCTCC TTAGTGGCTG GAATTACAGG CGCCTGCCAC CGCGCCTGGC
9481  TAATTTTTGT ATTTTTAGTA GAGACGGGAT TTCACCGTGT TGGCCAGGCT GGTCTCAAAC
9541  TCCTGACCTC AGGTGATCCA CCTGCCTCGG CCTCCCAAAG TGCTGGGATT ACAGGTGTGA
```

FIG. I (CONT.)

```
 9601  GCCATCGTGC CTGGGCTGGT TTTTTTGTTT TTTAGGGTTT TTTTTTTTTT TTTTTTTTGA
 9661  GATGGAATCT CACTCCGTCG TCCAGGCTGG GGTGCAGTGG TGCAATCTCG GCTCACTGCA
 9721  AACCTTCGCC TCCCAGTTG  AAGCAATTCT CCTGCCTCAG CCTCCCGAGT TGCTGGGACT
 9781  GTAGGCACAT GCACCACTC  CTGGCTAATT TTTGTATTTT TAGTAAAGAC AGAGTTTCCC
 9841  CATGTTGGCC AGGCTGGTCT CGAACTCCTG ATCTCAAGTG ATCTGCCCAA CTCAGCCTCC
 9901  CAAAGTGCTG GGATTACAGA CATGAGCCAA TGCACCCAGC CCAAATTTCC CCATTTTATA
 9961  AGACAACATT TATATTGGAT TAGGGACCCA CCCAATCCCA GTAGGACCAC ATCTTAACTA
10021  ATTACATCTG CAAGAACTCT TATCTCCAAA TAAGATCACA TGCTGAGTAC TGGGGGTTAG
10081  GGCTTCAACG TGTAAATTTT GGAAGGGACA CAGTTAAACC TTAACACCAG GTTTAAGGAC
10141  ATTTTCCCAG AGCTAGCCCC AGCCATGCTC AGTCTTTTCT GGAAGGTTCC AGACAATATC
10201  GCCTCCTGCT CTGGAATCTA GGCCTTGAAG AGGCAGCATA AGCCCACCTC TTATCCACCT
10261  CCAGGAGGTG GGCTTCTGGG GGTTCCTGGA CATCCACGTC CACCCACAGC ACAGACCCCC
10321  ATACCTCCCT GTCCTCTGCT CCCCAGAAAC AAACTGAAGC GCTGAAGCAG CGGGTGCAGA
10381  GGAAGCTGGA GCAGGTGTAC TACTTCCTGG AGCAGCAAGA GCATTTCTTT GTGGCCTCAC
10441  TGAGGACGT  GGGCCAGATG GTTGGGCAGA TCAGGAAGCC ATATGACACC CGCGTATCCC
10501  AGGACATCGC CCTGCTCGAT GCGCTGATTG GGAACTGGA  GGCCAAGGAG TGCCAGTCAG
10561  AATGGAACT  TCTGCAGGTG GGTGTGCCTG GGCCCGGCTT TCTTGGGTCC CCTGTGCCTA
10621  TCAGGATGCC TCAGGCTCCC AGCTCTGCCA TCAGCCGTGC TGGAACAAGT GGGTGAAGCC
10681  CTAAGCCCTA GGATAGGACT TGGTCTTGGT GACCCACAGT GCCTCTTGTG CCCAGACCCC
10741  TTTGATGAGG TCTCTCAGGA GCCCAGGGTG GCCTGGTATC CAGGGGATCT CTGCCATTTC
10801  CCAGAAGGGA TCAGCAGGGC TTGAGGGCCG TTCCATTGCA GGCCTCGCCA CCTGGGATGC
10861  CTGAATTCCC GTGGTTAGAA TTAGACTTGA AGAAAGGTGC TCCACTTCCA CTGACACCCT
10921  AGGGCAGGGA GCCCTGGTAA GTGCAGCGGG GAGCTAAAAG TCCAGGAGCC CAGAAGTAGA
10981  GGCCAGGAGT CAGCCCAGCC ACTAGGAGCC TGGTAACCGA CAGTTCCTT  CTTTTTCTC
11041  CTAGGACATT GGAGACATCT TGCACAGGTA CAGCGAGGTC CTGTGGTGTA CCCTGGGGTG
11101  TCTTGCAGAA AGCATATGGG GGAGACAGTC CCAGAAGGGA CCTGGAGGG  AGATGTTCCC
11161  AACCCCGGGG TCTGTGATTC CAGACTCCTC CTTTTTCTG  CAGCTTCCCA AAGCCTCTCT
11221  GGATTTGATA GGGAGAAGGG CATCTGGTCA GCAGGGAGGC TGCCCGGGTA TGGAGCTGCA
11281  GACTGGGAAG GGTGAATTCA GCCCATCCTG CTGAAACAAG ATGGAGGCTC CCTAAGAAAC
11341  CTTCCGAGTG CATTGTGTCC CGTGCAGTTC ATCTGATGAA GCTGCCCCT  TCAGGCCTAC
11401  TGGTGGCCTT GGAAGCTTG  TTTGGAGTGG AGCTGGCTA  AGCCCAGCAG GAAGGGGAGG
11461  GGAGGGAAGG GACAGGAAGA GGCTAAGCCT TAAAATCACC TGGGAGCTTT ACAAAATCCC
11521  GGTGTCCTTT TGTGTCTGGC TTCTTCACTT AGCATAATGT CTTCGGGCTT CATCCGTGTT
11581  GTAACGTGTA TCAGAATTTA TTTTCTTTTT ATGGCTGAAT CATAGTCCAG TGTGTGTTCA
11641  TACATTTTGC TTATCCATTC ATGGATATCG GGACTTCTTC TAACTTTTGG TTTGTGAATA
11701  ATGTTGCTAT GAACAAGGGT GTACAAATAT CTGCTTGAGA CCCTGCTTTG TTATTTGGG
11761  TACCTACCCA GAAGTGGAAC TGCGGGACCA TGTGGTTATC CTGTGTTTAA TTTTTTTTGA
11821  GGAACCACCA TCCTAATTCT CACAGGGCT  GCATCGCTTC ACATTCCCAC CAGCAGCACA
11881  CAGGGCTCC  AGTTTCTCCA CATCTTTGCC ATCACTTATT TTCTTCTGTT TCACTCTCTC
11941  TCTCTCTCTT TTTTTTGAA  GACAGCGTCT TGCTCTGTCA TCCAGGCTGG AGTGCAGTGG
```

FIG. I (CONT.)

```
12001 CGCGATCTTG GCTCACTACA ACCTCTGCCT CCCAGGTTCA AGGGATTCTC CCACCTCAGC
12061 CTCCCTAGTA GCTGGGACTA CAGGAGCGTG CCACCATGCC CAGCTAATTT TTTTGGTAGA
12121 CAGGGTTTCA CCATATTAGC CAGGCTGGTC TCAAACTCCT GACCTCAAGT GATCCACCCA
12181 CCTTGGCCTC CCAAAGCGCT GGGATTGCAG GCGTGAGCAC CGTGCCCAGC CATTTCTCTT
12241 TCCTTCCTTC CCTCCCTCCC TCCTTCCTT CCTTTCTTCC TTCCTTCCTT TCTTTTCTTC
12301 TTGAGACAAG GTCTCACTCC CATCACTAAG GCTGGAGAGC AGTGGCACAG TCACAGCTCA
12361 CTGCAGGCTC AGCTTCCTGG GCTCGGGTGA TTCTGAGTAG CTGGCATCCT GAGTAGCTGG
12421 GACTACAGGC ATGTGCTACC ACTTCCGGCT ACTTTTTTGT ATTTTTAATA GAGACAGGGT
12481 TTCGCCATGT TGCCCAAGCT GGACTTGAAC TCCTGGGCTC AAGCGATCCC ACTGCCCCGG
12541 CCTCCTGAAG TGCTAGGATT ACAGGCATGA GCCACCATAC CTGGTCTATT TTTTTCTGTT
12601 GTTGCTGTTT TTATAATAGC CATTCTAATG GATGTGAAGG GATATTTGT TGTGTGTGTT
12661 TTTTTTTCAT TTATTATCTT TTTATTTCAA TAGAAAGAAA GGGGTGTATA ATCAATTTGA
12721 CATAGATAAT TCTAGTAGAT AATATCAATG TCATTTTAAG TCCATTCTGA AAACTCCTTG
12781 TGGTTTTGAT ATCCATGTCT TTAAAGCACC CCAGTACATG ACAGTCTGTG GCCAAAGTTG
12841 AGGACCAGCA TTTAGACCTC TGAATCCAGG GAAGACTTTT CTTTGTGTAG CTCAGGCTGG
12901 GCTAGGTGTG CCTTGTGGAG AATGTAGTTC ATTCCAGCT CACGGGTACT TGGGCCACCC
12961 CCTCGCTCCG GCCTTCTCTG GTCAACAGTC TTTTGTCTCT AGGGCTAAGA CATGGCCTGT
13021 SCCTGCAAAG TGGACCACTC CTCAAGAGAT AAAACAAAAG ATCCAACTCC TCCACCAGAA
13081 GTCAGAGTTT GTGGAGAAGA GCACAAAGTA CTTCTCAGGT AGATGGCTT GGGAGAAGAT
13141 TGGAGGTGCA TGCTCACTTC CTCCCTAAGA TCCACATAGC CCAGAGCCCC TCACTTCCCT
13201 CCTCTTCCCC TGGTCTTGCT GACCTGCCTT CAACCTCTCC TCCATCTGTC CCTGGCTGAG
13261 GGACCTAACT CCAGCTTCTC TCTGCTCCCT TTCCCACATT TTAGAAACCC TGCGTTCAGA
13321 AATGGAAATG TTCAATGGTG AGTCCAGCGG TAATGGTGTG TGCTGGCCTG GGGTTGTTGC
13381 AGTGTTCCCT TGTGCTGTTG ACTTGAGGGG CCCTATTTAG AAGACAAAAA AAAAAACCAA
13441 ACACCTGGAG CAAAGGTAGG AGAAAGGTCA TGGCAGGCCC CCCAGGCTCT GTGCGTGACT
13501 CATTGACTGA GTTGACTCAT TAGACCACAG TCCCCAACAT GGCCTGGGTT CCTGGGAGGA
13561 ACGGGATTAT ACCCAACATA GCATGCAGGG CCCTAAGCAG GGGGTTCCTT GTCTTTCCTT
13621 GTTGTCAGGA CAGTGTAATT TAGCCCCTCT TAATGCTAAT GCTCAGGAAT TTTTTCCCTA
13681 TCTGATTTTT CTCCGTAGTT CCAGAGCTGA TTGGCGCTCA GGCACATGCT GGTAAGTGCC
13741 CAGATCAAGG CAAGTGGCCC TGGCCTGCTG GATCCCTGTG CTCTCCCCTA CCACGTTCCA
13801 GAAGAACTAC CCTGTCCCTG TTTCCTGCAG GTGGGGAGAA CCCTGTAGGG ATGTTGCCCA
13861 TGGACCCCTA CCTAGGTATT CAAATTTTCT TTGCAGTTAA TGTGATTCTG GATGCAGAAA
13921 CCGCTTACCC CAACCTCATC TTCTCTGATG ATCTGAAGAG TGTTAGACTT GGAAACAAGT
13981 GGGAGAGGCT GCCTGATGGC CCGCAAAGAT TTGACAGCTG TATCATTGTT CTGGGCTCTC
14041 CGAGTTTCCT CTCTGGCCGC CGTTACTGGG AGGTGGAGGT TGGAGACAAG ACAGCATGGA
14101 TCCTGGGAGC CTGCAAGACA TCCATAAGCA GGAAAGGGAA CATGACTCTG TGCCAGAGA
14161 ATGGCTACTG GGTGGTGATA ATGATGAAGG AAAATGAGTA CCAGGCGTCC AGCGTTCCCC
14221 CGACCCGCCT GCTAATAAAG GAGCCTCCCA AGCGTGTGGG CATCTTCGTG GACTACAGAG
14281 TTGGAAGCAT CTCCTTTTAC AATGTGACAG CCRGATCCCA CATCTATACA TTCGCCAGCT
14341 GCTCTTTCTC TGGCCCCTT CAACCTATCT TCAGCCCTGG GACACGTGAT GGAGGGAAGA
```

FIG. 1 (CONT.)

```
14401  ACACAGCTCC TCTGACTATC TGTCCAGTGG GTGGTCAGGG GCCTGAC[TGA] ATGCCCAACA
14461  CTGCATCTCT CTTCCTGCTT CTGGCCTTGT ATCTTGCATT CACACTCAAT AGTCACGGAA
14521  TGCCGACTAG GTGCTAGCTG CTATGGGAAA TGCMAAAATA ACAAAATAGT TACTGTGCCC
14581  ACGGAGCCCT ACCGATTAT  AGCAGAGGTA AGTTAGGAAC GAACATGTTA GTCAATCCGG
14641  GTGAAGACAT GTACTGATGA CACACCATGG ATTTCAGAGG AGGAAGTACG GAGTCGTTGC
14701  ATAATCCGCC CCTGGTGGGT GGCACTCTCA GGTGCTCCTG AACAGAAGAT TTGGCCCTCA
14761  TTTTCCCTCA GAACCCCACG GCAAGGATAT ATGTCCCCTT GTTCTCTCTG CTTCTGTCTT
14821  GAGGATATGG GAAGCCTAGA GAAACGCAAG CAGACTGGAT TGGGATAGAA GTATTTGTGT
14881  ACCTGGATTA ATGAACTATG ATTTTTTTTT TTTTTTTTTG AGACCAAATC TGCTCTGTG
14941  GCCCAGGCTG GAGTGCAGTG GCACGATCTC AGCTCACTGC AACCTCCACC TCCAGGTTC
15001  AAGCGATTCT CCTGCCTCAG CCTCCTGAGC AGCTGGGAT  TACAGGTGCG TGCCACCACA
15061  CCAGGCTGGT TTTCTTGTAT TTTTAGTAGA GACGGGGTT  TCACCATGTT AGCCAGGCTG
15121  GTCTCGAACT CCTGACCTCA GGTGATCCAC CCGCCTCAGC CTCCAAAGT  GCTGGGATTA
15181  CAGGCATGAG CCACTGTGCC CGGCCTATGA TTCTTTTTTT TTTTTTTTTT TGAGACAAAG
15241  TTTTGCTCTT GTCACCCAGG CTGGAGTGCA GTGGTGCAAT CTTGGCTCGC AACCTCCGCC
15301  TCCCAGGTTC AAGAGATTCT CCTGCCTCAG CCTCCAAGT  AGCTGGGATT ACAGGCGCCC
15361  GCCACCATGC CCGGCTAATT TTTTGCATTT TTAGTAGACA TGAGGTTTCA TCATGTTGGC
15421  CAGGCCGGTC TCAAACTCCT GACCTCAGGT GATGCACCCA CCTCAGCCTC CCAAAGTGCA
15481  GGGATTACAG GCATGAGCCA CCATGCCGGG CCATGATTCT TAAGAGAATT GACTGGCCT
15541  CATGAATAAA AAAATTAGAA AATCTGGTCA TTTGCATTTG TCACTCAATC ACTGTGGAAT
15601  CCCATTTCCC GACTGCATTT NCAGGAAGTC AGATGGGACT ACTGTCATGG AAAACATTT
15661  GGGCATGTTA TTTCCAAGTG TCAGATTATT CTGTCTTGGT TTGTATGGGA AAATCTGCGG
15721  GTTGTGGAAT ATTAGGTTCT ACTTCACACA CATCCCGTGC ATTTGTCCTT CATTTAAAGA
15781  GATGTAAAGG GGCCGGGCAT GGTGACTCAC ATCTGTAATC TCAGCATTTT GGGAGGCAAA
15841  GGCGGGTGGA TCGCCTGAGC CCAGGGATTG AGACCAGCTG GCAATGTGG  CGAAAACCCG
15901  TCTCTACAAA AAATACAAAA ATTAGCCATA GGGATGGGGG TGGAGGATG  GCTTGAGCGC
15961  AGGAGATCGA GGCTGCAGCA GTGAACTGAG ACTGCACTAC GGCAATCCAG CCTGGGCAAC
16021  AGAGTGAGTC CCTGTCTCCA AAAAGTGGAT GTTAGGAGTA CAAAAATCAA ATGAAGATTA
16081  GATCCAAACT CCTATGCCAA CTCCTCTGTC TTCACTACTA GAGTGTAGAT TAGACTCAGA
16141  TACTCCATGG CTATGATGAG AGCAGGTAAA CTTGCTGGGC TTTCCTCCAC GAGTTTTATT
16201  CTATAAGAGT AATCCACATC CCAGGACAGT TCACATGACC TACGGCTTAG CTGTTCCCTG
16261  CGGTGGGTCA TGTCTTATTC CCGATTCTCC CTTGTTATAA GCTTTTCATG AATATCTTTG
16321  TGTATATTTT CCACCACCTC ACCATATACA TATTTTTTTC TCCTGTGTTA TTCCTAAAAT
16381  GGTTCCTGAA TGTGAAATAT CTGATAATGC TTCCTACGGG TTGCCATACC ATCCTTTGCA
16441  AAGATTTTTA AAATATTTCA TGCCCAAAGC AATGACTGCC ATTTAAAATT TTTTTGCTGA
16501  TTTAATAGGG ATGTAATGAG GCCTTACTTC TGTTTTATTT CATTACCTGT TAATGAGGCT
16561  GTGAATTTTT CCATGTGAAT TTCTGCTTTT TGCTTCATTC TATGGAAATT GTACAGTTCC
16621  TTTGAATACT TGCTATTTGG AATCTACATA TTGAATTTCG TGTTTTGCTG TACTTCCTCA
16681  TTACATGGTT TTAGGCTGGG TGCGGTGCTC ACGCCTGAAA TCCCAACATT TTGGGAGCCG
16741  GAGGTGGGCA GGATCGGTTG GCAATCGAGG GTTTCGAGAC CGAGCCTGGG CAGACATGGC
```

FIG. 1 (CONT.)

16801 GAAACCTCGC CCTCTACCTA GAAAGATAAA CAAATTAGCG CAGGCAATGG TGGTGAGCAC
16861 CTGTAGTCCT AGCTGATAAG GTCTAGGTTG A

PYRIN GENE AND MUTANTS THEREOF, WHICH CAUSE FAMILIAL MEDITERRANEAN FEVER

This is a 35 U.S.C. §371 national phase application of, and claims priority to, international application PCT/US98/17255, filed Aug. 20, 1998, which claims priority, under 35 U.S.C. §119(e), to provisional application U.S. Ser. No. 60/056,217, filed Aug. 21, 1997, the entire contents of which are incorporated herein by reference.

BACKGROUND OF THE INVENTION

1. Field of the Invention

This invention relates to a novel genomic DNA sequence (MEFV) encoding a protein (pyrin) associated with familial Mediterranean fever (FMF). More specifically, the invention relates to the isolation and characterization of MEFV, and the correlation of mutations in MEFV with FMF disease.

2. Background of the Invention

Familial Mediterranean Fever (FMF) is a recessively inherited disorder characterized by dramatic episodes of fever, serosal inflammation and abdominal pain. This inflammatory disorder is episodic, with self-limited bouts of fever accompanied by unexplained arthritis, sterile peritonitis, pleurisy and/or skin rash. Patients often develop progressive systemic amyloidosis from the deposition of the acute phase reactant serum amyloid A (SAA). In some patients, progressive systemic amyloidosis can lead to kidney failure and death. The factors which incite an episode are unclear.

FMF is observed primarily in individuals of non-Ashkenazi Jewish, Armenian, Arab and Turkish background. Although rare in the United States, incidence of FMF in Middle Eastern populations can be as high as 1:7 in Armenian populations and 1:5 in non-Ashkenazi Jewish populations.

FMF attacks are characterized by a massive influx of polymorphonuclear leukocytes (PMNs) into the affected anatomic compartment. At the biochemical level, patients have been reported to have abnormal levels of C5a inhibitor (Matzner and Brzezinski, "C5a-inhibitor deficiency in peritoneal fluids from patients with familial Mediterranean fever," *N. Engl. J. Med.*, 311:287–290 (1984)), neutrophil-stimulatory dihydroxy fatty acids (Aisen et al, "Circulating hydroxy fatty acids in familial Mediterranean fever," *Proc. Natl. Acad. Sci. USA*, 2:1232–1236 (1985)), and dopamine β-hydroxylase (Barakat et al, "Plasma dopamine beta-hyroxylase: rapid diagnostic test for recurrent hereditary polyserositis," *Lancet*, 2:1280–1283 (1988)). Although linkage studies have placed the gene causing FMF (designated MEFV) on chromosome 16p (Pras et al., "Mapping of a gene causing familial Mediterranean fever to the short arm of chromosome 16," *N. Engl. J. Med.*, 326:1509–1513 (1992); Shohat et al., "The gene for familial Mediterranean fever in both Armenians and non-Ashkenazi Jews is linked to the α-globin complex on 16p: evidence for locus homogeneity," *Am. J. Hum. Genet.*, 51:1349–1354 (1992); Pras et al, "The gene causing familial Mediterranean fever maps to the short arm of chromosome 16 in Druze and Moslem Arab families," *Hum. Genet.*, 94:576–577(1994); French FMF Consortium, "Localization of the familial Mediterranean fever gene (FMF) to a 250 kb-interval in non-Ashkenazi Jewish founder haplotypes," *Am. J. Hum. Genet.*, 59:603–612(1996)), the genetic basis of FMF has not previously been identified.

Current treatment regimens for FMF include daily oral administration of colchicine. Although colchicine has been shown to cause near complete remission in about 75% of FMF patients and prevent amyloidosis, colchicine is not effective in all patients. Therefore, there is a need for new treatments for colchicine-resistant patients.

Additionally, there is a need for an accurate diagnostic test for FMF. Patients having FMF in countries where the disease is less prevalent often experience years of attacks and several exploratory surgeries before the correct diagnosis is made.

SUMMARY OF THE INVENTION

The invention provides a novel genomic nucleic acid sequence (MEFV) (SEQ ID NO:1), shown in FIG. 1, encoding the protein pyrin which is associated with familial Mediterranean fever (FMF). The corresponding cDNA sequence (v75-1) (SEQ ID NO:2) and encoded amino acid sequence (SEQ ID NO:3) are shown in FIG. 2. The invention is also directed towards fragments of the DNA sequence that are useful, for example, as hybridization probes for diagnostic assays or oligonucleotides for PCR priming. Additionally, the invention is directed towards the corresponding sequence for the RNA transcript and fragments thereof.

Another aspect of the invention provides the amino acid sequence for a protein associated with FMF. This protein is called pyrin, to connote its relationship to fever. The invention is directed towards both the full length amino acid sequence, fusion proteins containing the amino acid sequence and fragments thereof. These proteins are useful, for example, as antigens to produce specific anti-pyrin antibodies to be used as agents in diagnostic assays. Alternatively, the protein may be used in therapeutic compositions.

Mutations in pyrin result in FMF. Therefore, the invention is also directed towards mutants of the nucleic acid and amino acid sequences associated with FMF. In particular, the invention discloses three missense mutations, clustered in within about 40 to 50 amino acids, in the highly conserved rfp (B30.2) domain (SEQ ID NO:5) at the C-terminal of the protein. These mutants include M680I, M694V, K695R and V726A, each of which is associated with FMF.

Additionally, the invention includes methods for diagnosing a patient at risk for having FMF using the nucleic acid and/or amino acid sequences of the invention. Such methods include, for example, hybridization techniques using nucleic acid sequences, PCR-amplification of MEFV, and immunoassays using anti-pyrin antibodies to identify mutations is MEFV or pyrin which are indicative of FMF.

BRIEF DESCRIPTION OF THE FIGURES

FIG. 1 shows the genomic nucleic acid sequence for the gene associated with FMF;

FIG. 2 shows a cDNA sequence and deduced amino acid sequence corresponding to the gene associated with FMF;

FIG. 6 shows the alignment of multiple protein sequences with the C-terminal end of human pyrin.

DETAILED DESCRIPTION OF THE INVENTION

Figure 3:
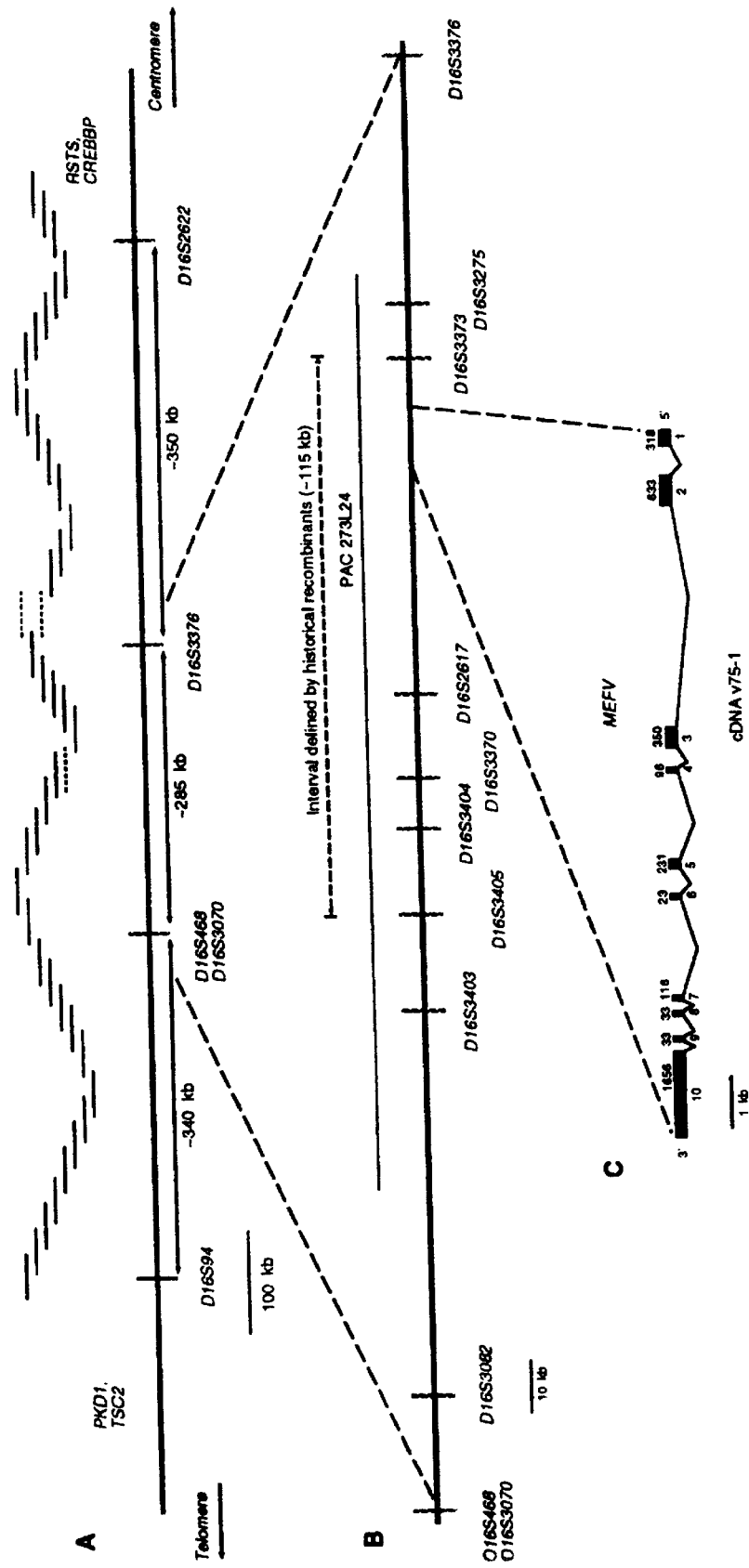
FIG. 3 is a schematic representation of MEFV on chromosome 16p13.3.

The invention relates to the nucleic acid sequence encoding a protein associated with familial Mediterranean fever (FMF). The genomic DNA sequence is designated MEFV. The corresponding cDNA sequence is designated as v75-1. The encoded protein is called pyrin, to connote its relationship to fever. The inventors have also discovered mutations in MEFV which are associated with FMF.

It is believed that pyrin is a nuclear factor that controls the inflammatory response in differentiated polymorphonuclear leukocytes (PMNs). In particular, pyrin is believed to be a negative autoregulatory molecule in PMNs. Knowledge of the genetic basis of FMF enables the production of diagnostic assays for FMF and treatments for FMF and other inflammatory diseases which are characterized by accumulation of PMNs, for example, acute infectious disease such as those caused by bacterial infection (e.g., Pneumococcal pneumonia), autoimmune diseases such as Sweets Syndrome or Behcet's disease, chronic arthritis, and the like.

The Nucleic Acid Sequence (MEFV)

The inventors have discovered the nucleic acid sequence for the gene associated with FMF. The nucleic acid sequence is found on chromosome 16p. Specifically, MEFV is located at 16p13.3 between the polycystic kidney disease gene (PKD1) and the tuberous sclerosis gene (TSC2) on the telomeric end, and the CREB-binding protein gene (CREBBP) on the centromeric end (see FIG. 3).

Figure 2:
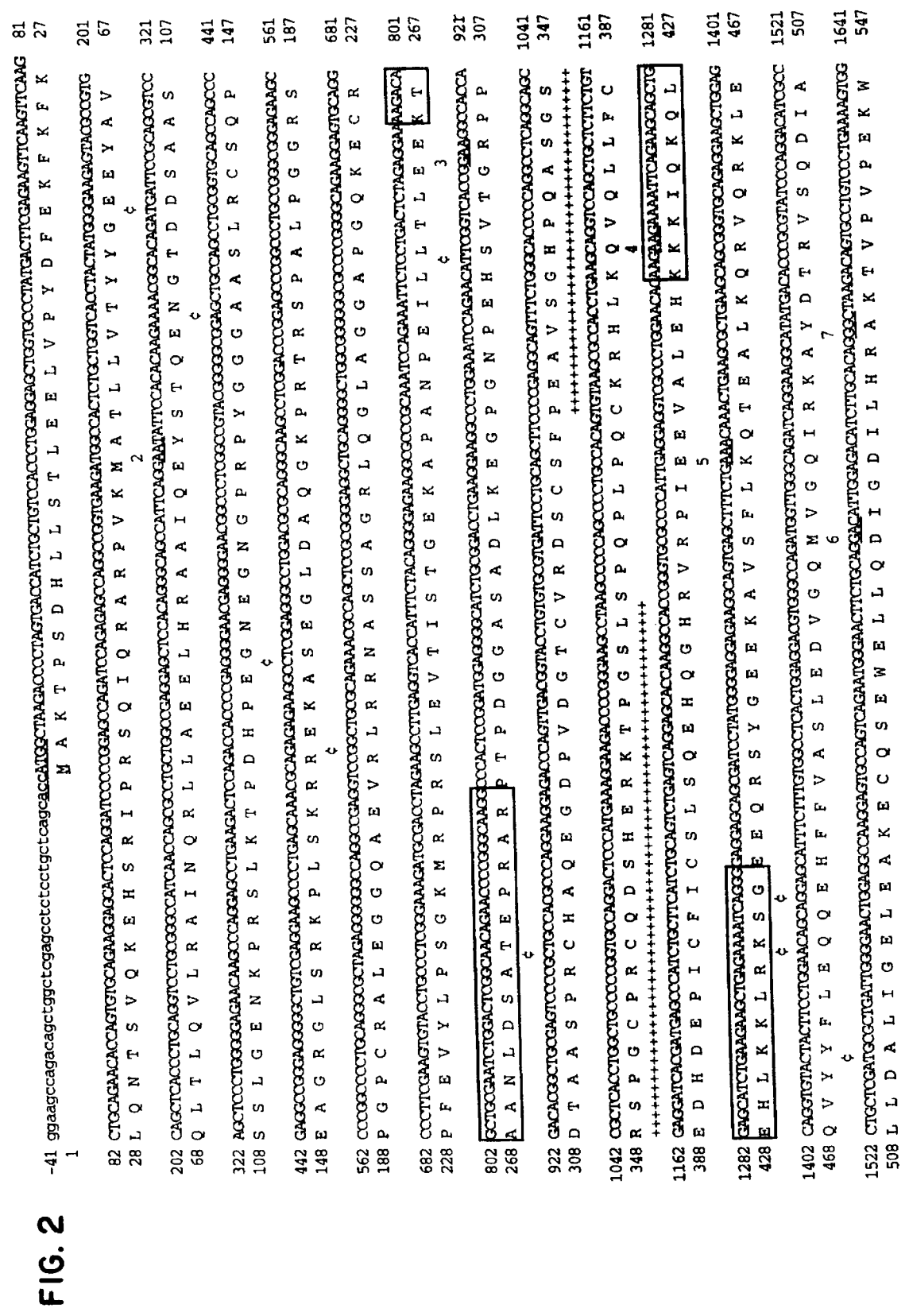
Figure 2:
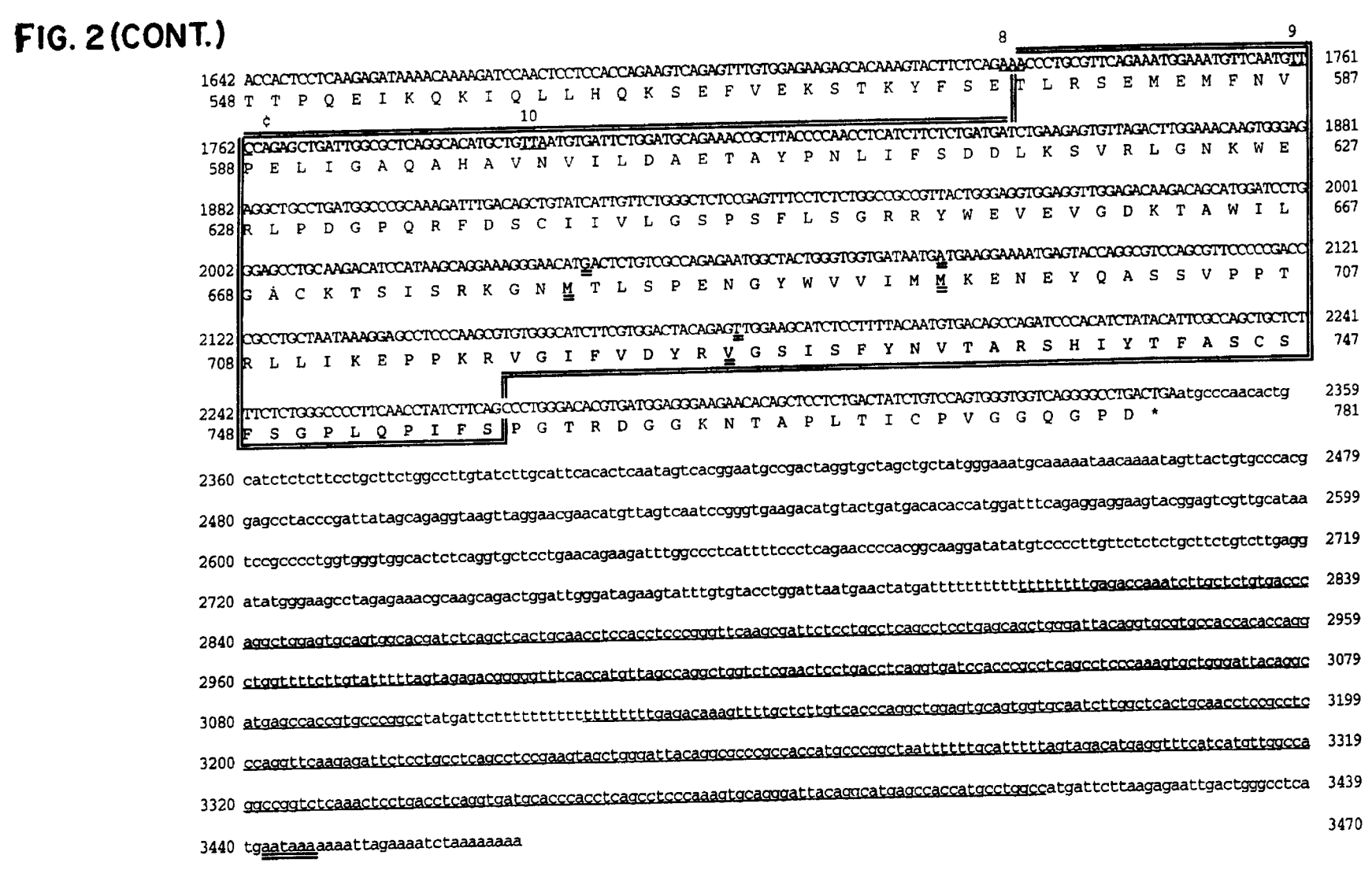

The genomic DNA sequence encoding pyrin (MEFV) (SEQ ID NO:1) is shown in FIG. 1. The start methionine and stop codon are boxed, while the exons are underlined. The cDNA sequence (v75-1) (SEQ ID NO:2) is shown in FIG. 2. In FIG. 2, the initial methionine and Kozak consensus sequences are underlined. The first boxed segment is a bZIP transcription factor basic domain. The second boxed segment is a Robbins/Dingwall consensus nuclear targeting signal. The segment indicated by +'s is a potential B-box zinc finger domain. The double-boxed region encloses a sequence which encodes a rfp, or B30.2, domain (SEQ ID NO:4). Within the double boxed region (the rfp or B30.2 domain), the nucleic acids encoding three FMF-associated mutations are double-underlined. Sites of synonymous single nucleotide polymorphisms are represented by the cents symbol "¢" above the sequence.

Although there is an excellent Kozak consensus sequence (Kozak, "Interpreting cDNA sequences: some insights from studies on translation," *Mamm. Genome*, 7:563–574 (1996)) at the initial methionine (accATGG), the reading frame remains open in the cDNA upstream. Because there are no splice-acceptor consensus sequences or in-frame methionines with good Kozak sequences before the first stop upstream in the genomic DNA, the initial methionine remains the most likely starting methionine.

The RNA Transcript

The estimated transcript size from the nucleic acid sequence shown in FIG. 2 is about 3503 nucleotides. The transcript size determined by Northern blotting is 3.7 kb. (See Example 4). The fact that the transcript size estimated from the sequence shown in FIG. 2 approximates the size of the transcript found in experimental procedures further indicates that the sequence shown in FIG. 2 is the full-length cDNA sequence.

The Encoded Protein

The inventors have also discovered the amino acid sequence for the protein associated with FMF (pyrin). Pyrin is predicted to be 781 amino acids in length and very positively charged. The pI is predicted to be greater than 8 (pI>8), in part due to the fact that lysine and arginine residues make up 13% of the amino acid composition.

The predicted amino acid sequence for pyrin (SEQ ID NO:3) is shown in FIG. 2. The boxed segment from amino acid 266 to 280 is a bZIP transcription factor basic domain. The boxed segment from amino acid 420 to 437 is a Robbins/Dingwall consensus nuclear targeting signal. The segment indicated by +'s between residues 375 and 407 is a potential B-box zinc finger domain. The region double-boxed from residue 577 to 757 is a rfp, or B30.2, domain (SEQ ID NO:5). The rfp (B30.2) domain is conserved (sequence identity 40–60%) in molecules as diverse as butyrophilin (a milk protein with probably receptor function; Jack and Mather, "Cloning and molecular analysis of cDNA encoding bovine butyrophilin, an apical glycoprotein expressed in mammary tissue and secreted in association with the milk-fat globule membrane during lactation," *J. Biol. Chem.*, 265:14481–14486 (1990)), A33 (a factor that binds polytene chromosomes in the newt; Bellini et al., "A putative zinc-binding protein on lampbrush chromosome loops," *EMBO J.*, 12:107–114 (1993)), and xnf7 (a factor that binds mitotic chromosomes in the frog; Reddy et al., "The cloning and characterization of a maternally expressed novel zinc finger nuclear phosphoprotein (xnf7) in Xenopus laevis," *Dev. Biol.* 148:107–116 (1991)) and, by an analysis with the SEG algorithm (Wootton, "Non-globular domains in protein sequences: automated segmentation using complexity measures," *Comput. Chem.*, 18:269–285 (1994)), most likely assumes a globular conformation. Within the double boxed region (the rfp or B30.2 domain), three of the amino acids that have been found mutated in FMF patients are double-underlined.

Expression

Pyrin is predominantly expressed in mature granulocytes and/or serosal cells. As shown in the Northern blots in FIG. 4, high levels of pyrin are expressed in peripheral blood leukocytes (granulocytes), but not in lymph nodes, bone marrow, monocytes, lymphocytes, spleen or thymus (See FIG. 4). Because granulocytes accumulate in tissues experiencing inflammation during a FMF episode, expression of pyrin in granulocytes is consistent with the clinical phenotype for FMF.

The restriction of pyrin to granulocytes, its apparent localization in the nucleus, and the phenotype associated with mutations tends to indicate that pyrin is a nuclear factor that controls the inflammatory response in differentiated PMNs. Additionally, the inventors found that pyrin shares homology with a number of molecules implicated in inflammation, such as rpt-1 (a known downregulator of inflammation). In view of the fact that FMF is a disease of excessive inflammation, and that pyrin shares homology to a known downregulator of inflammation, pyrin is believed to be a negative autoregulatory molecule in PMNs.

Homologies

Pyrin shares homology with a number of molecules implicated in inflammation including 52 kd Ro/SS A ribonucleoprotein (patients with systemic lupus erythematosus (SLE) and Sjögren's syndrome frequently make autoantibodies against this ribonucleoprotein); Staf-50 (an interferon-inducible transcriptional regulator; Tissot and Mechti, "Molecular cloning of a new interferon-induced factor that represses human immunodeficiency virus type 1 long terminal repeat expression," *J. Biol. Chem.*, 270:14891–14898 (1995)); and rpt-1 (a mouse downregulator of IL-2; Patarca et al., "rpt-1, an intracellular protein from helper/inducer T cells that regulates gene expression of interleukin 2 receptor and human immunodeficiency virus type 1," *Proc. Natl. Acad. Sci. USA,* 85:2733–2737 (1988)).

Figure 6:
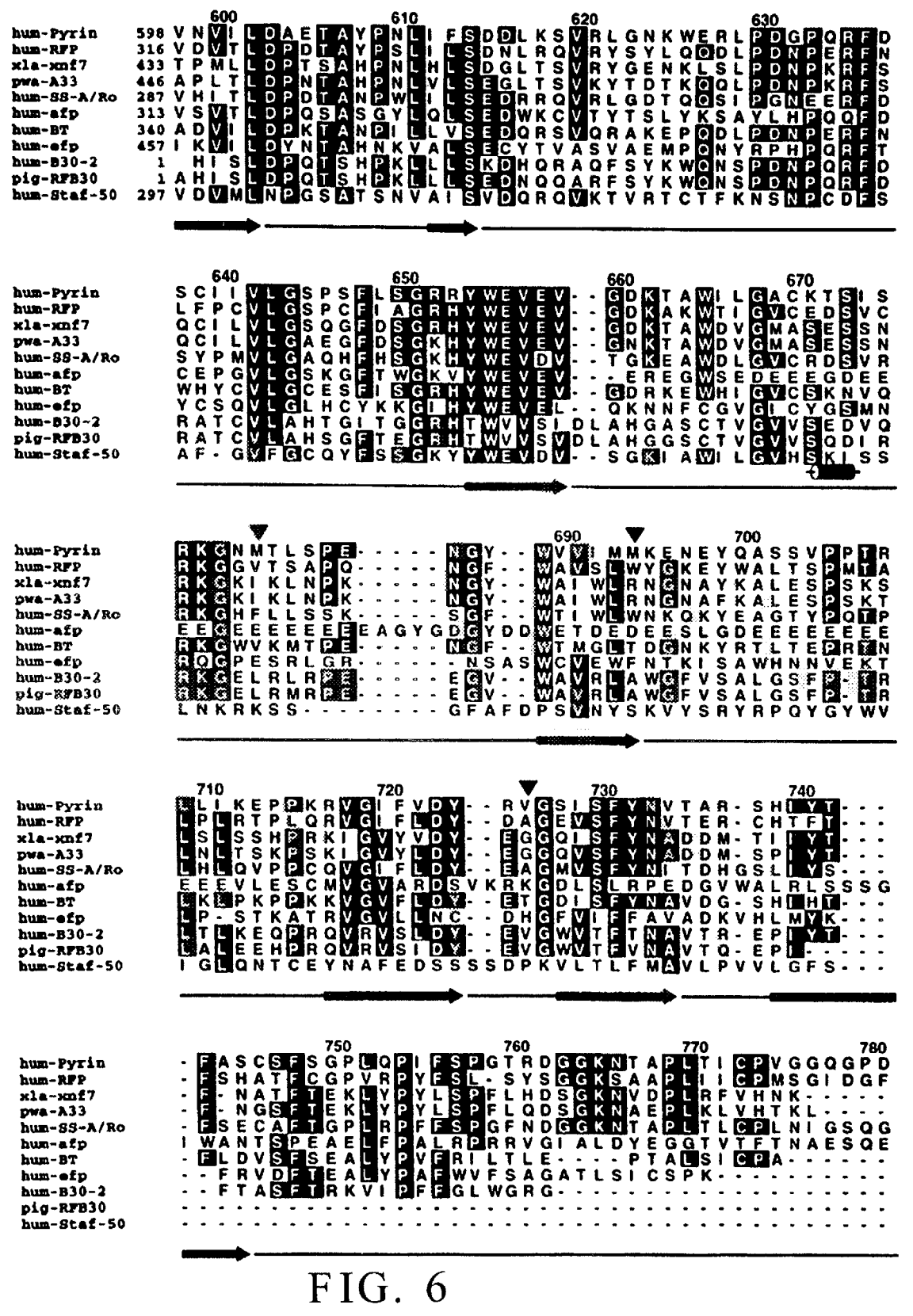

The homology between pyrin and rpt-1 is found in a domain extending from residues 385–550 on pyrin. Pyrin shows particularly high homology to many proteins, including 50 kdRo/SS A and Staf-50, at the C-terminal end, the rfp (B30.2) domain. FIG. 6 shows the alignment of the C-terminal end of human pyrin with multiple sequences having statistical similarity as assessed by BLAST (Altschul et al., supra). Search cutoffs used to identify homologs were a Karlin-Altschul score of two aligned sequences $\geq 70$ with a probability $\leq 10^{-3}$. At each position, residues occurring in a majority of the sequences are shown in inverse type. The numbering scheme at the top of the figure is based on the sequence of pyrin.

The B-box zinc finger and rfp (B30.2) domain combination observed in pyrin is also seen in 52 kd Ro/SS A and ret finger protein. The spacing between the B-box zinc finger and the rfp (B30.2) domain is highly conserved, suggesting that precise orientation of the two domains with respect to one another may be required for function.

Mutants

The inventors have also discovered missense mutations that are found in individuals affected with FMF, but not found in any of a large panel of normal control chromosomes. The missense mutations are clustered within about 40 to 50 amino acids (including residues 680 through 726) in the highly conserved rfp (B30.2) globular domain. It is believed that the mutations affect the secondary structure of this domain and result in a structural change that prevents the normal pyrin-mediated negative feedback loop.

A first mutation associated with FMF is a G → C transversion at nucleotide 2040 which results in the substitution of isoleucine for methionine (M680I). A second mutation is an A → G transition at nucleotide 2080 which results in the substitution of valine for methionine (M694V). A third mutation is a T → C transition at nucleotide 2177 which results in the substitution of alanine for valine (V726A). Additionally, the inventors have discovered a fourth mutation at position 695 which results in the substitution of Arginine for Lysine (K695R).

It is believed that phenotypic variation in FMF may be attributable to the differences between mutations. For example, the M694V mutation is very common in populations with the highest incidence of systemic amyloidosis (especially North African Jews). On the other hand, V726A is seen in populations in which amyloid is less common (Iraqi and Ashkenazi Jews, Druze and Armenians).

Figure 5:
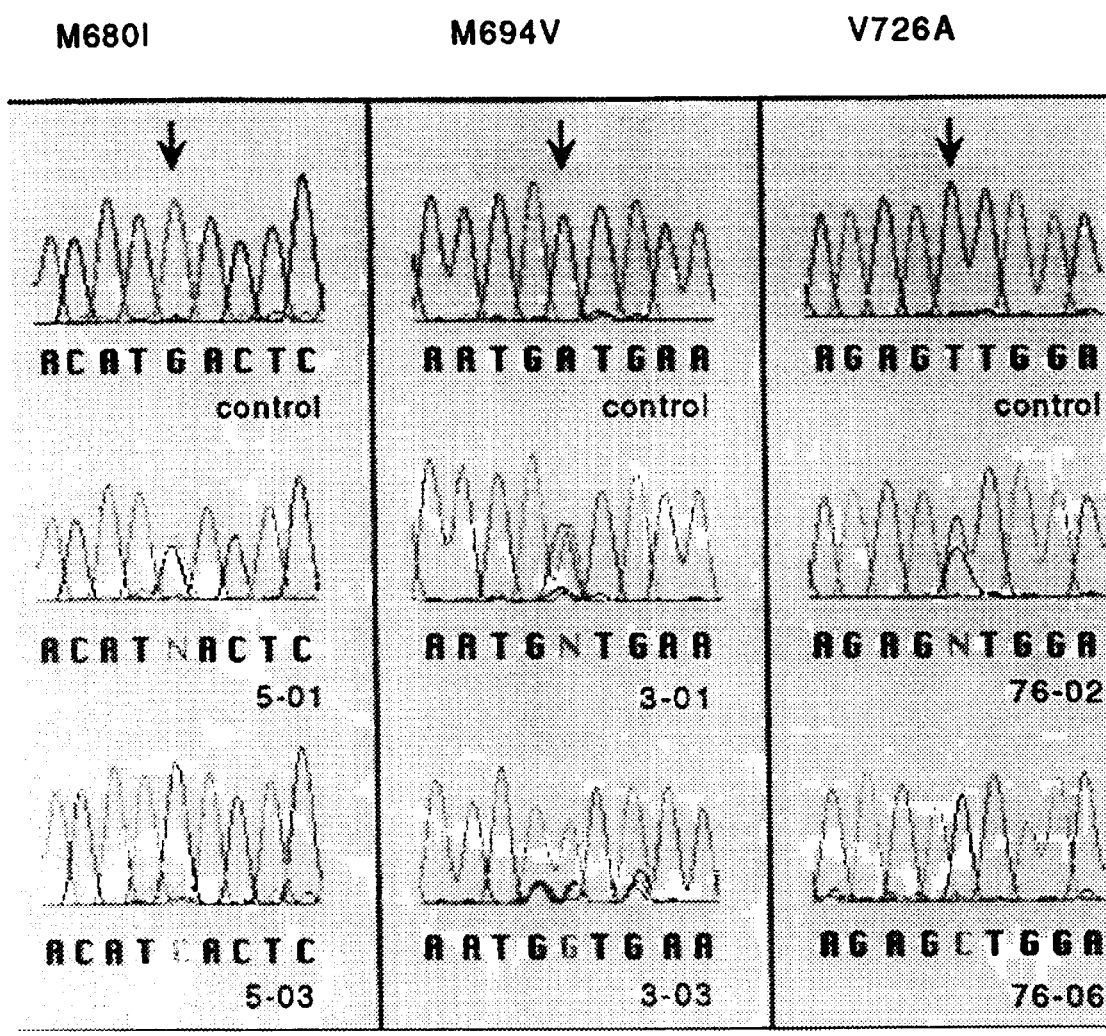
FIG. 5 shows the DNA sequences of the M680I, M694V and V726A mutants.

FIG. 5 shows DNA sequence electropherograms, produced by amplifying exon 10 genomic DNA and sequencing, which demonstrate the M680I, M694V, and V726A substitutions. For each mutation, individuals who are homozygous for the normal allele are shown at the top, heterozygotes between the normal and mutant allele are shown in the middle, and homozygotes for the mutation are shown at the bottom.

None of these mutations result in a truncated protein. This is consistent with the periodic nature of the inflammatory attacks in FMF. Other diseases with periodic episodes are associated with a protein that functions adequately at steady state, but decompensates under stress, such as sickle cell anemia (Weatherall et al., "The hemoglobinopathies," In *The Metabolic and Molecular Bases of Inherited Disease*, Scriver et al, eds., New York, McGraw-Hill, pp. 3417–3484 (1995) and hyperkalemic periodic paralysis (Ptacek et al., "Identification of a mutation in the gene causing hyperkalemic periodic paralysis," *Cell*, 67:1021–1027 (1991)).

Diagnostic Methods

The sequences provided by this invention can be used in methods for diagnosis of risk for developing FMF. As used herein, an individual is "at risk" for developing FMF when the individual has a mutant MEFV nucleic acid sequence which results in expression of mutant pyrin, particularly where the amino acid mutation occurs in the highly conserved rfp (B30.2) C-terminal domain. Mutations include substitutions of one nucleic acid with a different nucleic acid. In contrast, a patient having wild type MEFV nucleic acid sequence expressing wild type pyrin is not at risk for developing FMF. As used herein, "wild type" refers to a dominant genotype which naturally occurs in the normal population (i.e., members of the population not afflicted with familial Mediterranean fever). Thus, methods for identifying an individual's specific nucleic acid or amino acid sequence are useful for determining risk of FMF. Specifically, a method for determining whether an individual's nucleic acid sequence encodes a wild type or mutant pyrin is useful in determining whether the individual is at risk for developing FMF.

Many methods for analysis of an individuals nucleic acid or amino acid sequences are known to those of skill in the art, and include, for example, direct sequencing, ARMS (amplification refractory mutation system), restriction endonuclease assays, oligonucleotide hybridization techniques, and immunoassays. While some commonly used procedures are exemplified below, the inventors are aware that other methods are available and include them within the scope of their invention.

Southern Blot Techniques

In Southern blot analysis, DNA is obtained from an individual and then separated by gel electrophoresis. Following electrophoresis, the double stranded DNA is converted to single stranded DNA, for example, by soaking the gel in NaOH. The DNA is then transferred to a sheet of nitrocellulose. The DNA is then contacted with a labeled probe. For example, labeled probe can be applied to the nitrocellulose after it dries. As used herein, a "probe" is a nucleic acid sequence that is complementary to the sequence of interest. The probe can be either a DNA sequence or an RNA sequence. Preferably the probe is about 8 to 16 nucleotides in length. A radioactive label, such as $^{32}P$ is an example of a suitable label. Other suitable labels include fluorophores or an enzyme which catalyzes a color producing reaction (e.g., horse radish peroxidase). Because the probe has complementary sequence to the DNA sequence of interest, it will hybridize to the specific DNA sequence. As used herein, "hybridize" means that the probe will form a double-stranded molecule with the specific DNA sequence by complementary base pairing under conditions of high stringency (e.g., 65° C.; 0.1×SSC; Sambrook et al., *Molecular Cloning. A Laboratory Manual*, Cold Spring Harbor, N.Y.: Cold Spring Harbor Press (1989)). After the probe is allowed to hybridize to the DNA, excess probe is washed away. The hybridized DNA is easily visualized from the labeled probe using known techniques. Hybridization of the probe indicates that the sample DNA contains a sequence that is complementary to the labeled probe. In a preferred method, hybridization probes are designed from the MEFV nucleic acid sequences, and particularly, from the C-terminal MEFV sequence encoding the rfp (B30.2) globular domain.

It is often desirable to amplify the sample DNA for more efficient analysis. Polymerase chain reaction (PCR) can be used to amplify the DNA. PCR is a technique that is well known to one of skill in the art. An exemplary method includes developing oligonucleotide primers that hybridize to opposite strands of DNA flanking the MEFV gene. As used herein, a "primer" is a short nucleotide sequence which is complementary to a DNA sequence flanking the DNA sequence of interest. Preferably the primer is about 15 to 20 nucleotides in length. The specific fragment defined by the primers exponentially accumulates by repeated cycles of denaturation, oligonucleotide primer annealing and primer extension. In a preferred embodiment, the PCR primers amplify the region encoding the rfp (B30.2) globular domain. The amplified domain can then be analyzed by hybridization or screening techniques.

For example, oligonucleotide primers are developed to amplify MEFV, the rfp (B30.2) domain, or a fragment thereof, such as the preferred 40 to 50 amino acid fragment of the rfp (B30.2) domain discussed above. Suitable oligonucleotide primers, such as "Exon 10A Forward and Reverse", "Exon 10B Forward and Reverse", and "Exon 10B Forward and Exon 10A Reverse", are shown in Example 1.

Northern Blot Techniques

The presence of a wild type or mutant RNA transcript may be determined by Northern Blot Techniques, following a procedure similar to that outlined for the Southern Blot Technique.

Western Blot Techniques

The presence of a wild type or mutant protein from the highly conserved C-terminal rfp (B30.2) region can be detected by immunoassay, for example by Western Blot Techniques. In this procedure, a tissue sample is obtained from an individual and separated by gel electrophoresis. Following electrophoresis, the proteins are then transferred to nitrocellulose. The proteins are then contacted with a labeled probe, for example, by applying the labeled probe to the nitrocellulose after it is dried. Suitable probes include labeled anti-pyrin antibodies, preferably those antibodies specific for an epitope in the highly conserved C-terminal rfp (B30.2) domain. Exemplary labels include radioactive isotopes, enzymes, fluorophores and chromophores. Because it is believed that mutants in the highly conserved C-terminal domain alter the secondary structure of the domain, an antibody specific for the wild-type protein should not bind to or recognize a protein having a mutation in this highly conserved region. Conversely, an antibody specific for a mutant protein does not recognize or bind to the wild type. After excess antibody is rinsed away, the presence of the specific protein/antibody complex is easily determined by known methods, for example by development of the label attached to the anti-pyrin antibody, or by the use of secondary antibodies.

Sequencing Techniques

Alternately, DNA, RNA or protein obtained from an individual can be sequenced by known methods, and compared to the wild type sequence. Mutations recognized in the sequence, particularly, in the rfp (B30.2) domain indicate risk for developing FMF.

ARMS

ARMS (amplification refractory mutation system) is a PCR based technique in which an oligonucleotide primer that is complementary to either a normal allele or mutant allele is used to amplify a DNA sample. In one variation of this method, a pair of primers is used in which one primer is complementary to a known mutant sequence. If the DNA sample is amplified, the presence of the mutant sequence is confirmed. Lack of amplification indicates that the mutant sequence is not present. In a different variation, the primers are complementary to wild type sequences. Amplification of the DNA sample, indicated that the DNA has the wild type sequence complementary to the primers. If no amplification occurs, the DNA likely contains a mutation at the sequence where hybridization should have occurred. A description of ARMS can be found in *Current Protocols in Human Genetics,* Chapter 9.8, John Wiley & Sons, ed by Dracopoli et al. (1995).

Restriction Endonuclease Assays

Restriction endonuclease assays can also be used to screen a DNA sample for mutants, such assays are used by Pras et al., "Mutations in the SLC3A1 transporter gene in Cystinuria," *Am. J. Hum. Genet.,* 56:1297–1303 (1995). Briefly, a DNA sample is amplified and then exposed to restriction endonucleases that will or will not cleave the DNA depending on whether or not a mutation is present. After cleavage, the size of restriction fragments are observed to determine whether or not cleavage occurred.

Oligonucleotide Hybridization Techniques

Hybridization techniques, such as dot blots, are known to one of skill in the art and can be used to determine whether a DNA sample contains a specific sequence. In a dot blot, a DNA sample is denatured and exposed to a labeled probe which is complementary for a wild type sequence or a mutant sequence. Hybridization of a probe that is complementary to the wild type sequence (a "wild type probe") indicates that the wild type sequence is present. If the wild type probe does not hybridize to the DNA in the sample, the wild type sequence is not present. In a variation of this technique a probe that is complementary to a know mutant sequence can be used. A discussion of allele specific oligonucleotide testing can be found in *Current Protocols in Human Genetics,* Chapter 9.4, supra.

Immunological Assays

An immunological assay, such as an Enzyme Linked Immunoassay (ELISA), can be used as a diagnostic tool to determine whether or not an individual is at risk for developing FMF. One of skill in the art is familiar with the procedure for performing an ELISA. Briefly, antibodies are generated against native or mutant pyrin. This can be accomplished by administering a native or mutant protein to an animal, such as a rabbit. The anti-pyrin antibodies are purified and screened to determine specificity. In one representative example of an immunoassay, wells of a microtiter plate are coated with the specific anti-pyrin antibodies. An aliquot of a sample from a patient to be analyzed for pyrin is added in serial dilution to each antibody coated well. The sample is then contacted with labeled anti-pyrin antibodies. For example, labeled anti-pyrin antibodies, such as biotinylated anti-pyrin antibodies, can be added to the microtiter plate as secondary antibodies. Detection of the label is correlated with the specific pyrin antigen assayed. Other examples of suitable secondary antibody labels include radioactive isotopes, enzymes, fluorophores or chromophores. The presence of bound labeled (biotinylated) antibody is determined by the interaction of the biotin with avidin coupled to peroxidase. The activity of the bound peroxidase is easily determined by known methods.

Production of Pyrin

The nucleic acid sequence encoding wild type or mutant pyrin can be used to produce pyrin in cells transformed with the sequence. For example, cells can be transformed by known techniques with an expression vector containing v75-1 cDNA sequence operably linked to a functional promoter. Expression of pyrin in transformed cells is useful in vitro to produce large amounts of the protein. Expression in vivo is useful to provide the protein to pyrin-deficient cells. Examples of suitable host cells include animal cells such as bacterial or yeast cells, for example, *E. coli.* Additionally, mammalian cells, such as Chinese hamster ovary (CHO) cells can be used. Human cells, such as SW480 colorectal adenocarcinoma can also be used as host cells.

Due to degeneracy of the genetic code, most amino acids are encoded by more than one codon. Therefore, applicants recognize, and include within the scope of the invention, variations of the sequence shown in SEQ ID NO: 1. For example, codons in a DNA sequence encoding pyrin can be modified to reflect the optimal codon frequencies observed in a specific host. Rare codons having a frequency of less than about 20% in known sequences of the desired host are preferably replaced with higher frequency codons.

Additional sequence modifications are known to enhance protein expression in a cellular host. These include elimination of sequences including spurious polyadenylation signals, exon/intron splice site signals, transposon-like repeats, and other well characterized sequences which may be deleterious to gene expression. The G-C content of a sequence may be adjusted to levels average for a given cellular host, as calculated by reference to known genes expressed in the host cell. Where possible, the sequence is modified to avoid predicted hairpin secondary mRNA structures. The genomic sequence might additionally be modified by the removal of introns.

Transgenic Animals

The nucleic acid sequences encoding pyrin, both wild-type and mutant, provided in this application are useful for the development of transgenic animals expressing pyrin. Such transgenic animals are used, for example, to screen compounds for treating FMF or inflammation.

Useful variations of a transgenic animal are "knock out" or "knock in" animals. In a "knock out" animal, a known gene sequence, such as the sequence encoding pyrin, is deleted from the animal's genome. Experiments can be performed on the animal to determine what effect the absence of the gene has on the animal. In a "knock in" experiment, the wild type gene is deleted and a mutant version or a gene from another organism is inserted therefore. Experiments can be performed on the animal to determine the effects of this transition.

Kits

The invention is also directed towards a kit for diagnosing risk of FMF. A suitable diagnostic kit includes a nucleic acid sequence encoding wild-type pyrin and at least one nucleic acid sequence encoding mutant pyrin. An alternative kit includes an anti-pyrin antibody which binds to wild-type pyrin and at least one anti-pyrin antibody which binds to mutant pyrin. A kit also preferably contains at least one pair of amplification primers capable of amplifying a nucleic acid sequence encoding pyrin. Preferably, the primers amplify a nucleic acid sequence encoding a rfp (B30.2) domain of pyrin.

The present invention may be better understood with reference to the following examples. These examples are intended to be representative of specific embodiments of the invention, and are not intended as limiting the scope of the invention.

EXAMPLES

The DNA samples used in the following examples were extracted from whole blood or from Epstein-Barr virus-transformed lymphocytes by standard techniques. The DNA was obtained from forty-four families of non-Ashkenazi Jewish descent (18 Moroccan, 14 Libyan, 5 Tunisian, 2 Egyptian and 5 Iraqi) and 5 Arab/Druze families (identified and sampled at the Chaim Sheba Medical Center in Tel-Hashomer, Israel). Additionally, twelve Armenian families were recruited from Cedars-Sinai Medical Center in Los Angeles. One Ashkenazi/Iraqi Jewish family was also studied.

The diagnosis of FMF in all families was according to established clinical criteria (Sohar et al., "Familial Mediterranean fever: a survey of 470 cases and review of the literature," *Am. J. Med.,* 43:227–253 (1967)).

Example 1

Positional Cloning

A positional cloning approach was used to clone a new cDNA (v75-1) from the FMF candidate region on chromosome 16p13.3. Mutational analysis indicates the v75-1 is the gene (designated MEFV) expressing pyrin, mutations of which are associated with FMF disorder.

Publicly available polymorphic markers (discussed below) were used to narrow the candidate region on chromosome 16p to an approximately 1 Mb interval between D16S94 and D16S2622 (Sood et al., "Construction of a 1-Mb restriction mapped cosmid contig containing the candidate region for the familial Mediterranean fever locus (MEFV) on chromosome 16p13.3," *Genomics,* 42:83–95 (1997)) lying between the polycystic kidney disease (PKD1) and tuberous sclerosis (TSC2) genes on the telomeric end, and the CREB-binding protein (CREBBP) gene on the centromeric end (see FIG. 3). Because physical maps constructed around these genes did not extend into the MEFV region, a contig was constructed which spanned the candidate region.

Attempts to construct a mega YAC (yeast artificial chromosome) contig spanning the MEFV candidate region were unsuccessful due to the instability of YAC clones from this region of chromosome 16. Instead, a cosmid map was assembled by iterative screening of a flow sited chromosome 16 specific cosmid library. D16S246 was the telomeric starting point of the chromosomal walk. Identification of recombinants at D16S2622 enabled us to use this microsatellite marker as the centromeric boundary (Sood et al., 1997, supra).

Observed recombinations of microsatellite markers in a panel of 61 families defined a critical region of 285 kb (D16S468-D16S3376).

By analysis of the genomic sequence from this region, two new microsatellites, D16S3404 and D16S3405 (FIG. 3B), were found in the center of the D16S3082-D16S3373 interval. In one non-Ashkenazi Jewish family, evidence of a historical recombination event between D16S3404 and D16S3405 in the highly conserved non-Ashkenazi Jewish haplotype (designated haplotype A) was observed. Therefore, the region telomeric of D16S3405 (and 4 candidate genes encoded therein) were excluded from further consideration. The discovery of the two new microsatellites and the historical recombination event further refined of the candidate interval to the centromeric-most 115 kb.

A combined strategy of exon amplification, direct cDNA selection, and single-pass sequencing led to the isolation of 9 full length cDNA clones. The furthest centromeric cDNA clone, v75-1, was isolated by solution hybridization of a leukocyte cDNA library with biotinylated oligonucleotide probes derived from two exons trapped from PAC 273L24.

Exon Trapping

PAC (P1 artificial chromosome) clone 273L24 (Genome Systems; St. Louis) includes the centromeric-most 115 kb. Therefore, exon trapping was performed on PAC clone 273L24. Exon trapping was performed essentially as described by Buckler et al., "Exon amplification: a strategy to isolate mammalian genes based on RNA splicing," *Proc. Natl. Acad. Sci. USA,* 88:4005–4009 (1991). Essentially, PAC clone 273L24 was partially digested with Sau 3AI (commercially available, for example, from New England Biolabs). The reaction products were size fractionated by agarose gel electrophoresis and DNA fragments 2 kb and larger were isolated from the gel. Fifty ng of partially digested DNA was ligated with 10 ng of exon trapping vector pSPL3 (Exon Trapping System; Life Technologies, Gaithersburg, Md.) that had been previously cleaved with Bam HI (commercially available) and dephosphorylated with calf intestinal alkaline phosphatase (Promega, Madison, Wis.). Ligation products were electroporated into E. coli DH12B (Life Technologies, Gaithersburg, Md.) The electroporated cells were cultured en mass in LB broth with 200 mg/ml ampicillin for 16 hours at 37° C. with shaking.

DNA prepared from the culture was used to transfect COS-7 cells (ATCC 30-2002) using lipofectACE reagent (Life Technologies, Gaithersburg, Md.). Total RNA was isolated from transfected COS-7 cells with Trizol reagent (Life Technologies) followed by ethanol precipitation.

First strand cDNAs of transcription products from pSPL3 were primed with the oligonucleotide SA2 (Exon Trapping System; Life Technologies, Gaithersburg, Md.). Specific amplification of trapped exons was as follows: PCR primed with oligonucleotides SA2 and SD6 (Exon Trapping System; Life Technologies, Gaithersburg, Md.) was performed, followed by digestion of the PCR products with Bst XI (commercially available).

A second PCR reaction using the digestion products was primed with oligonucleotides dUSD2 and dUSA4 (Exon Trapping System; Life Technologies, Gaithersburg, Md.). The resulting DNA fragments were cloned into pAMP10 vector (Exon Trapping System; Life Technologies, Gaithersburg, Md.) and sequenced. Two hundred clones were sequenced and 20 independent exons were identified by visual inspection and hybridization to DNA fragments from the FMF critical region, with several exons identified more than one time.

Oligonucleotides for Exon Amplification

Oligonucleotides used to amplify pyrin exons were as follows (all oligo sequences are given 5' to 3'):

Exon 1 forward, AAC CTG CCT TTT CTT GCT CA; (SEQ ID NO:6)

Exon 1 reverse, CAC TCA GCA CTG GAT GAG GA; (SEQ ID NO:7)

Exon 2A forward, ATC ATT TTG CAT CTG GTT GTC CTT CC; (SEQ ID NO:8)

Exon 2A reverse, TCC CCT GTA GAA ATG GTG ACC TCA AG; (SEQ ID NO:9)

Exon 2B forward, GGC CGG GAG GGG GCT GTC GAG GAA GC; (SEQ ID NO:10)

Exon 2B reverse, TCG TGC CCG GCC AGC CAT TCT TTC TC; (SEQ ID NO:11)

Exon 3 forward, TGA GAA CTC GCA CAT CTC AGG C; (SEQ ID NO:12)

Exon 3 reverse, AAG GCC CAG TGT GTC CAA GTG C; (SEQ ID NO:13)

Exon 4 forward, TTG GCA CCA GCT AAA GAT GGC; (SEQ ID NO:14)

Exon 4 reverse, TCT CCC TCT ACA GGG ATG AGC; (SEQ ID NO:15)

Exon 5 forward, TAT CGC CTC CTG CTC TGG AAT C; (SEQ ID NO:16)

Exon 5 reverse, CAC TGT GGG TCA CCA AGA CCA AG; (SEQ ID NO:17)

Exon 6 forward, TCC AGG AGC CCA GAA GTA GAG; (SEQ ID NO:18)

Exon 6 reverse, TTC TCC CTA TCA AAT CCA GAG; (SEQ ID NO:19)

Exon 7 forward, AGA ATG TAG TTC ATT TCC AGC; (SEQ ID NO:20)

Exon 7 reverse, CAT TTC TGA ACG CAG GGT TT; (SEQ ID NO:21)

Exon 8/9 forward, ACC TAA CTC CAG CTT CTC TCT GC; (SEQ ID NO:22)

Exon 8/9 reverse, AGT TCT TCT GGA ACG TGG TAG; (SEQ ID NO:23)

Exon 10A forward, CCA GAA GAA CTA CCC TGT CCC; (SEQ ID NO:24)

Exon 10A reverse, AGA GCA GCT GGC GAA TGT AT; (SEQ ID NO:25)

Exon 10B forward, GAG GTG GAG GTT GGA GAC AA; (SEQ ID NO:26)

Exon 10B reverse, TCC TCC TCT GAA ATC CAT GG. (SEQ ID NO:27).

Direct cDNA selection

Direct cDNA selection was used to isolate 2 full-length cDNA clones (Parimoo et al., "cDNA selection: efficient PCR approach for the selection of cDNAs encoded in large chromosomal DNA fragments," *Proc. Natl. Acad. Sci. USA*, 88:9623–9627 (1991). Cosmids, BAC (bacterial artificial chromosome) and P1 clones in the FMF candidate region were biotinylated using BioPrime (Life Technologies, Gaithersburg, Md.). cDNAs were prepared from combined mRNA from fetal brain, fetal liver, and human lymph node by reverse transcription and ligation of an EcoRI/NotI adaptor to second strand cDNAs.

cDNAs were directly hybridized to biotinylated templates which were recovered using streptavidin-labeled magnetic beads. Conditions for blocking, hybridization, binding and elution of cDNAs from magnetic beads (Dynal) were as described by Parimoo et al., supra. After two rounds of selection, eluted cDNAs were amplified with CUA-tailed EcoRI/NotI adaptor primers and subcloned into the pAMP10 vector (Life Technologies, Gaithersburg, Md.) to yield libraries of selected cDNAs.

Recombinant clones were arrayed on blots. Clones that hybridized to either repetitive or ribosomal sequences were excluded from further analysis. To confirm their origin, unique clones were individually hybridized to EcoRI digests of cosmid/BAC/P1 DNAs and DNAs from chromosome 16-specific human-hamster hybrid lines. Clones were then hybridized to each other and were binned into groups. Representative clones of each group were hybridized to multiple tissue Northern blots and sequenced.

cDNA Identification by Solution Hybridization

Following the protocol provided in the Gene Trapper kit, the furthest centromeric cDNA, clone v75-1, was isolated by solution hybridization of a leukocyte cDNA library with biotinylated oligonucleotide probes derived from 2 exons trapped from PAC 273L24. Solution hybridization was carried out using the GeneTrapper cDNA Positive Selection System (Life Technologies, Gaithersburg, Md.).

Two trapped exons, v66 and v75, were used as starting material. PCR screening of Superscript cDNA libraries (Life Technologies, Gaithersburg, Md.) derived from human brain, liver, leukocytes, spleen, and testis were used to determine the tissue-specific expression of these exons. GeneTrapper experiments were performed with sense and antisense primers from both exons, assuming both orientations of these exons in the putative transcript.

The following oligonucleotides were synthesized and PAGE-purified:

v66GTI: AAG CTC ACT GCC TTC TCC TC; (SEQ ID NO:28)

v66GT2: GAG GAG AAG GCA GTG AGC TT; (SEQ ID NO:29)

v75GTI: GAC TTG GAA ACA AGT GGG AG; (SEQ ID NO:30)

v75GT2: CTC CCA CTT GTT TCC AAG TC. (SEQ m NO:31).

Oligos were biotinylated, hybridized to single-stranded DNA from the leukocyte cDNA library (one primer per reaction), followed by cDNA capture using paramagnetic streptavidin beads and repair using the corresponding non-biotinylated oligos. Colony hybridization of lifts using $^{32}$P-dCTP end-labeled oligos was used to identify positive clones. Gel-purified inserts from these clones were hybridized to cosmid contig blots in order to distinguish cDNA clones mapping to the FMF region from false positive clones due to homologous domains. All positive clones were identified by the primers v66GT2 and v75GT2, and no clones were identified by the other set of primers.

Characterization of cDNA v75-1

The translated v75-1 cDNA sequence is shown in FIG. 2. The exon-intron structure deduced from the genomic sequence of two cosmids is depicted in FIG. 3C. Shaded boxes represent exons; introns are drawn to scale. The numbers above the boxes represent the size of the exons in bp. The numbers below the boxes reflect the order of the exons with 1 being the most 5'.

Although there is an excellent Kozak consensus (Kozak, supra) at the initial methionine, the reading frame remains open in the cDNA upstream. There are no splice-acceptor consensus sequences or in-frame methionines with good Kozak sequences before the first stop upstream in the genomic DNA. Additionally, the transcript size by Northern blot is 3.7 kb. The estimated transcript size from cDNA is 3503 nucleotides. Therefore, the sequence appears to be the full-length sequence.

Example 2

Mutational Analysis

Three different v75-1 mutants of FMF carrier chromosomes in multiple ethnic groups are not seen in a panel of almost 300 normal control chromosomes. This indicates that v75-1 is a cDNA of MEFV, the gene associated with FMF.

Three missense mutations were identified in exon 10 of v75-1 (FIG. 5) after screening a total of 165 individuals from 65 families. All three mutations are clustered within 46 amino acids of one another in the highly conserved rfp (B30.2) globular domain at the C-terminal end of the predicted protein. The first mutation, is a G ⊗ C transversion at nucleotide 2040 in which methionine is replaced by isoleucine (M680I). This mutation was observed in the homozygous state in the affected offspring of a single Armenian family. The second mutation is a A ⊗ G transition at nucelotide 2080 in which methionine is replaced by valine (M694V). This was observed in a large number of affected individuals bearing four apparently distinct disease associated haplotypes. The third mutation is a T ⊗ C transition at nucleotide 217 which substitutes alanine for valine (V726A). It was observed in affected individuals bearing the C haplotype in a Druze family and in other FMF patients and carriers bearing this haplotype. An additional mutation in which lysine is replaced by arginine at positions 695 (K695R) was observed in an American FMF patient of Northern European ancestry.

Direct sequencing of RT-PCR products or amplified exons from the 8 cDNAs telomeric to v75-1 failed to identify disease-associated mutations.

It is extremely unlikely that the substitutions in v75-1 are actually polymorphisms in tight linkage disequilibrium with "real" mutations on a nearby gene. This hypothesis would require that there be 3 such v75-1 polymorphisms on 3 different haplotypes, each in perfect linkage disequilibrium with the mutations on the "real" FMF gene. While not impossible, such a scenario is at least unnecessarily complex. It is also unclear where such a closely linked gene would be located. The historical recombinants at the 5' (centromeric) end of v75-1 exclude the interval between D16S33 73 and v75-1. On the telomeric side, the 5' end of a novel zinc finger gene is located within 10 kb of the 3' end of v75-1, but thorough screening has revealed no mutations in this later gene (data not shown). Moreover, there are no trapped exons, direct selected cDNAs or expressed sequence tag (EST) hits that map to the interval between them. Finally, and most importantly, the observation of normal chromosomes that bear disease-associated microsatellite and SNP haplotypes but do not have the M680I, M694V or V726A mutations is strong evidence that these are not just haplotype-specific polymorphisms.

Mutation Detection by Fluorescent Sequencing

The entire coding region was sequenced, plus splice cites, in individuals representing seven microsatellite haplotypes. Approximately 100 ng of genomic DNA template was used in PCR reactions to amplify exons and flanking intronic sequences according to the supplier's recommendations for AmpliTaq Gold (Perkin Elmer, Branchburg, N.J.) and Advantage-GC Genomic PCR Kit (Clontech, Palo Alto, Calif.).

The PCR primers were tailed with one of the following sequences:

21 M13 forward: GTA AAA CGA CGG CCA GT; (SEQ ID NO:32)

28 M13 reverse: CAG GAA ACA GCT ATG ACC AT; (SEQ ID NO:33)

40 M13 forward: GTT TTC CCA GTC ACG ACG. (SEQ ID NO:34).

After amplification, reactions were run on 1% agarose gels and gel purified using either QIAquick gel extraction kit (QIAGEN, Santa Clarita, Calif.) or Microcon/Micropure/Gel Nebulizer system (Amicon, Beverly, Mass.). Alternatively, PCR products were column purified with Microcon-100 (Amicon). Purified amplicons were sequenced with dye primer chemistry (PE Applied Biosystems, or Amersham, Cleveland, Ohio). Sequencing reactions were ethanol precipitated and run on an ABI 377 automatated sequencer. Sequence data were analyzed with either Autoassembler 1.4 (PE Applied Biosystems, Branchburg, N.J.) or Sequencher 3.0 (Gene Codes Inc., Ann Arbor, Mich.).

Example 3

Protein Modeling

The deduced amino acid sequence was examined. Two overlapping nuclear targeting signals were detected using the PSORT algorithm (Nakai and Kanehisa, "A knowledge base for predicting protein localization sites in eukaryotic cells," *Genomics*, 14:897–911 (1992). The first nuclear targeting signal is a four residue pattern composed of a histidine and three lysines. The second is a Robbins/Dingwall consensus (Robbins et al., "Two interdependent basic domains in nucleoplasmin nuclear targeting sequence: identification of a class of bipartite nuclear targeting sequence," *Cell*, 615–523 (1991). A bZIP transcription factor basic domain (Shuman et al., "Evidence of changes in protease sensitivity and subunit exchange rate on DNA binding by C/EBP, *Science,* 249:771–774 (1990) was identified using a PROSITE search (Bairoch et al., "The PROSITE database, its status in 1997," *Nucleic Acid Res.,* 25:217–221 (1997)). The spacing of cystine and histidine residues between residues 375 and 407 (denoted by plus signs in FIG. 2) resembles a B-box type zinc finger domain (Reddy et al., "A novel zinc finger coiled-coil domain in a family of nuclear proteins," *Trends Biochem. Sci.,* 17:344–345 (1992)).

Example 4

Localizing Expression of the Protein

The tissues in which v75-1 is expressed are highly consistent with the clinical phenotype for FMF. Based on the nature of the inflammatory infiltrate and the anatomic localization of inflammation in FMF, MEFV gene expression might be predicted to be observed in granulocytes and/or serosal cells. Multiple tissue northern blots demonstrated high levels of expression in peripheral blood leukocytes, primarily in mature granulocytes, but not in lymph nodes, spleen or thymus which are comprised largely of lymphocytes.

Figure 4A:
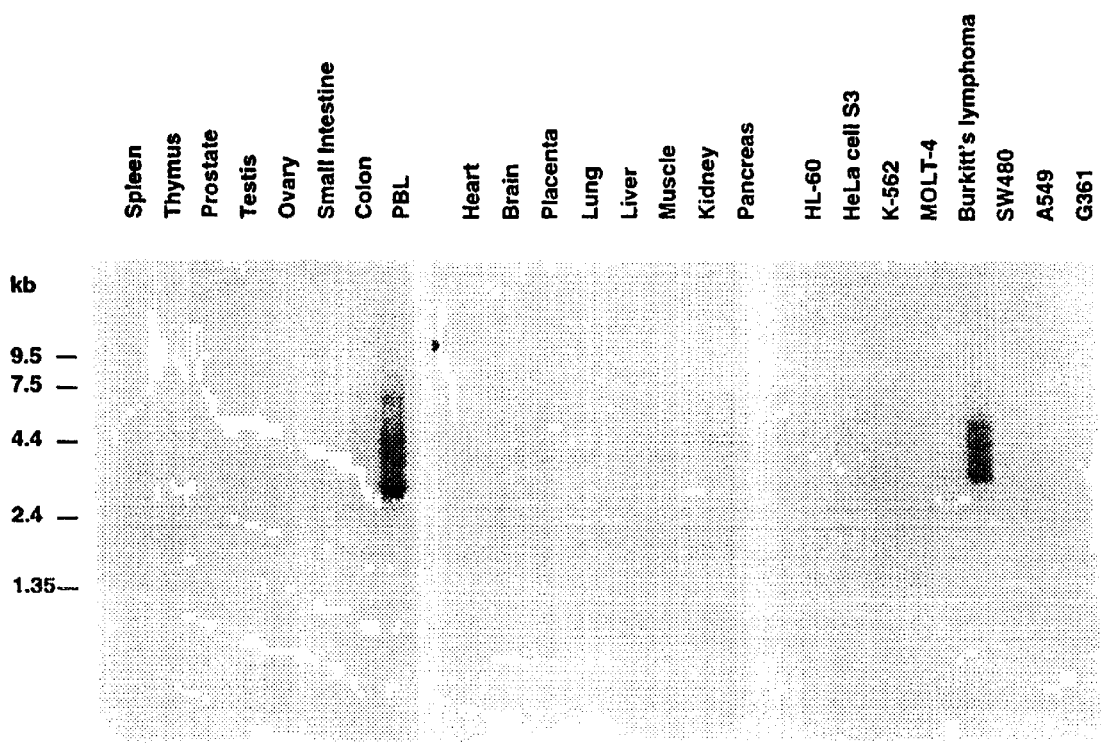
FIG. 4 show the expression profile of V75-1.

FIG. 4 shows the expression profile for the v75-1 gene. FIG. 4A shows the results of hybridization of a probe derived from exon 2 on multiple tissue Northern blots. A 3.7 kb transcript was found in peripheral blood leukocytes (PBL) and colorectal adenocarcinoma (SW480). The presence of the transcript in peripheral blood leukocytes compare favorably with the symptoms associated with FMF. The detection of the 3.7 transcript in colorectal adenocarcinoma is unexplained.

Figure 4B:
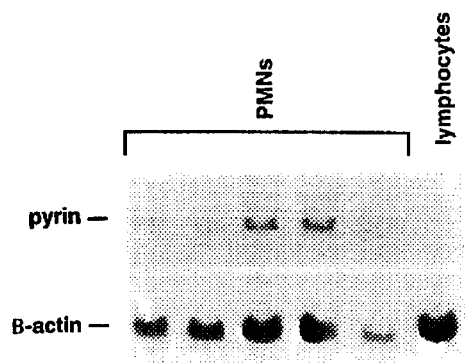

FIG. 4B shows hybridization of the same exon 2 probe on Northern blots with mRNA from purified Polymorphonuclear leukocytes (PMNs) and lymphocytes. PMN lanes represent preparations from different individuals. A β-actin control can be seen at the base of the gel.

The following abbreviations were used in FIG. 4: HL-60 (promyelocytic leukemia); K-562 (erythroleukemia); MOLT4 (lymphoblastic leukemia); A549 (lung carcinoma); and G361 (melanoma).
Northern Blot Analysis To determine transcript size and level of expression in various tissues, multiple tissue Northern blots (Clontech) were hybridized with probes derived from various exons of the gene. These exons were amplified and purified as part of the sequencing protocol for mutation analysis. Larger exons (2, 5, and 10) were labeled by random-priming using Stratagene Prime-It Kit and $^{32}$P-dCTP (ICN). Hybridization and washing of blots were essentially as described in Sambrook et al., *Molecular Cloning. A Laboratory Manual,* Cold Spring Harbor, N.Y.: Cold Spring Harbor Press (1989), except using Hybridisol I (Oncor) prepared hybridization buffer. Hybridization was detected by autoradiography, with 4 hour exposures. Northern blots with mRNA from highly purified peripheral blood lymphocytes, PMNs, and monocytes were the kind gift of Drs. H. Lee Tiffany and Harry Malech.

Example 5

Homologies to Other Proteins

FIG. 6 shows the alignment of the rfp (B30.2) domain of pyrin with homologous proteins. The following abbreviations are used in FIG. 6: hum-RFP (RET finger protein; SWISS-PROT P14373); xla-xnf7 (nuclear phosphoprotein xnf7, Xenopus laevis; PIR A43906); pwa-A33 (zinc-binding protein A33, Pleurodeles walt1; SWISS-PROT Q02084); hum-SS-A/Ro (52 kDa RO protein;

SWISS-PROT P19474); hum-afp (acid finger protein; GenBank U09825); hum-BT (butyrophilin; GenBank U90552); hum-efp (estrogen-responsive finger protein; PIR A49656); hum-B30-2 (B30-2 gene; PRF 2002339); pig-RFB30 (ring finger protein RFB30, Sus scrofa; EMBL Z97403); hum-Staf-50 (transcription regulator Staf-50; IR A57041).

The invention has been described with reference to various specific and preferred embodiments and techniques. However, it should be understood that many variations and modifications may be made while remaining within the spirit and scope of the invention. All publications in this specification are indicative of the level of ordinary skill in the art to which this invention pertains. All publications and patent applications are herein incorporated by reference to the same extent as if each individual publication or patent application was specifically and individually indicated by reference.

What is claimed is:

1. An isolated nucleic acid sequence, comprising the coding sequence of SEQ ID NO: 2 or a nucleic acid encoding SEQ ID NO: 3.

2. An isolated nucleic acid sequence consisting of the sequence of SEQ ID NO: 1.

3. An isolated nucleic acid sequence selected from the group consisting of SEQ ID NO:6, SEQ ID NO:8, SEQ ID NO: 10 and SEQ ID NO:12.

* * * * *

SEQUENCE LISTING

```
<160> NUMBER OF SEQ ID NOS: 45

<210> SEQ ID NO 1
<211> LENGTH: 16891
<212> TYPE: DNA
<213> ORGANISM: homo sapiens
<220> FEATURE:
<221> NAME/KEY: misc_feature
<222> LOCATION: (0)...(0)
<223> OTHER INFORMATION: n = a, t, c, or g

<400> SEQUENCE: 1
tatttttgta ttttagtaga gatggggttt actgtgttgg ccaggctggt cttgtactcc      60
caacctgagg tgatccaccc acctcggcct cccaaagtgc tgggattaca ggcgttagca     120
ctgtgccctg cccccaacat gtaacttctg ttagcttcaa agccacctct ggggccctgc     180
```

-continued

| | |
|---|---|
| accacatatg agctgaagga cacccgtgcc ttttcacccg tgtagctcca gcatcttggc | 240 |
| acactgtcta gaatgttcaa tgaatgtgca cggaagagca ttctggctcc agggagcgag | 300 |
| gactgagtca gctctgggaa cagatgagtc aggctggtgg tccaggcatt gcttttcaag | 360 |
| tccttcatgt ggctggaaga accagtcaac tggaaccgga tcaacagggg tgatggcatg | 420 |
| gcaagagtta tctcctggca gtgcccttct ggcctcactt gccttcttgg gccaggaaag | 480 |
| gcaaagctca caggactgta ttcagtgccc accccttccc ccgtcctgtg ccattggctc | 540 |
| tggaaggtcc ctgaaacccc gagtctggag gagaacagtt gaccagcagg gcgggccctc | 600 |
| agcatagtcc tctctgttcc cactcacccg ctctgccagc cccagatcct ggcaggaagg | 660 |
| aagattggag ggggtgtctg gaatccaatc ccagaccttc ccttgcagac ttgcccatct | 720 |
| gtctgtggtc tagtgtggag gcgaggtcca gggtttggga ggggtgtggg ggcacatgtc | 780 |
| tgccaaggca tggagccctc ccagctggaa aatcctctga acctgtaaga agagaacaca | 840 |
| gccggcatgg acacacccct tacccttagtc tcagttccca ccaagacaca gagcatttcc | 900 |
| tgtgccttttt ccgctatttc acaacctgcc ttttcttgct caccaaggac agaggcttct | 960 |
| tttcctacca gaagccagac agctggctcg agcctctcct gctcagcacc atggctaaga | 1020 |
| cccctagtga ccatctgctg tccacccctgg aggagctggt gccctatgac ttcgagaagt | 1080 |
| tcaagttcaa gctgcagaac accagtgtgc agaaggagca ctccaggatc ccccggagcc | 1140 |
| agatccagag agccaggccg gtgaagatgg ccactctgct ggtcacctac tatgggggaag | 1200 |
| agtacgccgt gcagctcacc ctgcaggtcc tgcgggccat caaccagcgc tgctggccg | 1260 |
| aggagctcca cagggcagcc attcagggta agcgggccca ggcctcctcc tcatccagtg | 1320 |
| ctgagtgctg gctgctttgt gggaaggggg accaggagct cagagcagct cactctgacc | 1380 |
| tggggattgg gagtctcagg tctaccaaaa tccagatgac tttagttcag gaacgtccct | 1440 |
| ttcttcactc tggcctttgg aactgggtta gtaaacttcc ttcaggctcc taatgggttt | 1500 |
| tttaagaagc aggtcagggt cacgaaaggc aggagctgga cacctgttc tttgagactt | 1560 |
| cttcactaca tttatgatta atactcatgt cagacaaaca tctctaggtt agcaaaaagg | 1620 |
| gattgctatg caatcatatg aacggggttg gtatagaatc ttctcagtgc tgttcaccat | 1680 |
| gttggccagc tggtctcga actcctgacc tcaagtgatc ctcccgcctc agcctcccaa | 1740 |
| agtgctggga tttcagacat aggccaccgt gcccggctta ttttatttt taaagcgtat | 1800 |
| aatctgggtt ttgctgacct gtgtaagatc ttatttgaaa cagttgtcct gcttaaaacg | 1860 |
| tttgaaaagt actatttgag aaatataggc taggcatggt ggctcacact tataaataat | 1920 |
| ctcagcactt tgggaggcta aggtgggtgg attgctagag ctcaggagtt tgagaccagc | 1980 |
| ttgggcaaca tggtgaaacc ctgtctctac caaaaataca aaaaaatgag ccaggcgtgg | 2040 |
| tagcacacac ctgtattttc agctattgaa aaaacagaaa acaggctgag gtgagaggat | 2100 |
| tgcttgagcc tgggaggcag aggttgcagt gagctgagat cacatcaggg caacagagca | 2160 |
| agatcctgtc tcaaaaaata aaataagaga gagagaaata catagcaaca tcaagcatgt | 2220 |
| tcttactgaa tggtaattga ctgccattgt ctagtctggg nagtcctgaa cttttgtttt | 2280 |
| tgagatggag tcttgctctg tcactcaggc tggagtgcag tggcccgatc tcagctcnct | 2340 |
| gcaacctcca catcccgggc tcaagcgatt tcatgcctc agcctcccga gtagctggga | 2400 |
| ctacaggtgc gcaccaccgc gtctggctga gtttcttatt tttagtagga acggggtttt | 2460 |
| gccatgttgg ccaggctggt ctcgaactcc tgacctcaaa tgatcctccc accttggcct | 2520 |
| ctggagaagc tgggattaca ggcatgcgca ccacgctcag cttattttttg tattttttagt | 2580 |

```
agagacgggg tttcaccctg ttggtcttga actcctgatc tcaggtgatc ctcccgcctc   2640
ggcctcccag agtgccggga atacaggcat gagccaccgc gcccggcccg ttgttttcct   2700
caatttctaa actttaatat ccaaggggat tctctctcct ctgccctgaa tcttgggccc   2760
taaacgtggg acagcttcat cattttgcat ctggttgtcc ttccagaata ttccacacaa   2820
gaaaacggca cagatgattc cgcagcgtcc agctccctgg gggagaacaa gcccaggagc   2880
ctgaagactc cagaccaccc cgaggggaac gaggggaacg gccctcggcc gtacggggc    2940 ggagctgcca gcctgcggtg cagccagccc gaggccggga gggggctgtc gaggaagccc   3000
ctgagcaaac gcagagagaa ggcctcggag ggcctggacg cgcagggcaa gcctcggacc   3060
cggagcccgc cctgccgggg cgggagaagc cccggcccct gcagggcgct agagggggc    3120 caggccgagg tccggctgcg cagaaacgcc agctccgcgg ggaggctgca ggggctggcg   3180
gggggcgccc cggggcagaa ggagtgcagg cccttcgaag tgtacctgcc ctcgggaaag   3240
atgcgaccta gaagccttga ggtcaccatt tctacagggg agaaggcgcc cgcaaatcca   3300
gaaattctcc tgactctaga ggaaaagaca gctgcgaatc tggactcggc aacagaaccc   3360
cgggcaaggc ccactccgga tggaggggca tctgcggacc tgaaggaagg ccctggaaat   3420
ccagaacatt cggtcaccgg taaattgtgt tctttccaac tttatatcgg ctgcagagaa   3480
agaatggctg gccgggcacg atagctcatg cctgtaatcc cagcgctttg ggaggccagg   3540
gcgggaggat tgctggaggc caagactttg agaccagcct ggtgaatgta gtgagacccc   3600
cgccatctct ataaacgaaa ttaaaaaaat aaaaacccaa aggttgggca gggcgtggta   3660
gctctcgcct gtaatcccag agctttgaga ggcctgcacg ggaggatctc ttgaccccag   3720
gagttccata ctagcctagg caacacagtg agaccccatc tctacaaaat acaatagtgg   3780
cacgcgcctg tagtcccagc tgctcgggtt cacttgagca gacggagttc caggctacag   3840
tgagctgagg atcatgccac tgcacaccag cctgagcaac gtagccagac tcacttctac   3900
aaaactaaaa aaaaaattag ctgggtatgg tggcacacgc ctgtaattct agccactcag   3960
gaagctgagg caggaggatt gcttgagcca gggagttcca ggctgcagtg agctgaggat   4020
gtgccactgc actccggcct gggcaacaga gcaagaccct gtctcttaaa cattttgggg   4080
ggaaaaaaaa agaaagaaag aatgtccgat tgaaaaaggc aatcaggtgt tatcagtggc   4140
caaagaatgg agaaggggag ctcacctctg caggcgtctg cttgccaggg atgggaggca   4200
gggcgatttt agagtccagg gaggggaagg gagataggta agcaggccca gggcagggtt   4260
ccatatgtgc aggcgctgtc cccagcatgc ttcttcctac atcgcattca aacaaaccct   4320
tctccatctt ctttagggga ggacccttta gcttataacc atgtgtaaat gatcctaagg   4380
taactggaag tcacctcttc cagtttgcac tggttttgct ctgatcttaa cttcctctgg   4440
tttttggcaa gggatcagga ggctccaggc catctggatt tttttaagca gctgtcccta   4500
taggtaaaga gactaaaaaa aaactgtaaa agaaaatgc  caccagttta gagggtaccg   4560
aggctatcca ggtgacaatt ccatgctcgt ggtgggggca gcattcagaa acacactttc   4620
cttttttttc ctccttttt   tttttgagac agagtctcag tctgtctccc atgctggagt   4680
gcagtagtgt gagcacagtt tactgcagcc tcaacctcct aggctcaagc gatcctccca   4740
cctcagcctt ccaagtagct gagactatag gtgctcacca ccacacctgg ttaatttttt   4800
tttttttttt tgtattttt  tgtagttacga ggactgtcta tgttgcccag gctggttttg   4860
aactcttggg ctcaagcgat cccccgcctt agcctctaaa agtgctagga tttcaggtgt   4920
```

-continued

| | | | | | |
|---|---|---|---|---|---|
| gagtcactac | acccagccta | tggaacacac | tttccaatgc | attgttggct | ggagaggaga | 4980 |
| aatcacagca | ctcaaggagg | agaaatagaa | ttgggggtcc | aggccgggtg | cggtggctca | 5040 |
| tacctgtaat | cccagcactt | tgggaggcca | atggggggcgg | atcacctgag | gtgaggagtt | 5100 |
| cgagaccagc | ctgccaacat | ggtgaaacgc | catctctact | aaaaatacta | aatttgctgg | 5160 |
| gcgtggtggc | gggtgtccat | aatcccagct | actcagaagg | cttcgaggca | ggagaattgc | 5220 |
| ttgaaccgag | gaggcagagg | ttgcagtgag | ccaagatcat | gccactgcac | tctagcctgg | 5280 |
| gcgacaagag | caaaactctg | tctcaaaaaa | aaaaaaaaa | aagaattggg | agtccaggga | 5340 |
| cccctgagac | ctgggagggg | aaaggatgtg | gtatgctgca | tgagtcttca | aatccagaag | 5400 |
| tccctgggtc | ttccagtgag | aaaggaccct | gggatctgga | aaacctagca | tccttaggaa | 5460 |
| tagtgacctg | aaaagtactg | aagtatttcc | cccctaattt | tcttttatcc | ctactgtatt | 5520 |
| tttttttaatt | ttttttttttt | tttagatatg | gggtcttgct | atgttgccca | ggttggtctc | 5580 |
| gaactcctga | tctcaaacaa | tcctcccatc | tttgcctccg | aaactgctgg | gattacaggt | 5640 |
| gtgcaccact | gcaccaggtc | cccactgtat | ttatatcatt | gggattcctg | ggtgtcttct | 5700 |
| agggccgctt | cgttaatctg | atgcaggctt | agaccctgaa | aaatgcatat | atgcacagct | 5760 |
| tcacaaatgt | cacatcaaat | ttcaggtagt | tcttggacac | tctgaagacc | atctttagaa | 5820 |
| tccaagggt | ttatggacac | caggtagaaa | atctgggaa | gactggttaa | aaatactccc | 5880 |
| tctcacaata | acctcacagc | aatgcatcat | catgggttg | agattctacc | attgcctttc | 5940 |
| tctcagcaga | aagaaaagcc | tattggctaa | agtcctaact | atctactgct | gaggtagtca | 6000 |
| ttaaaattat | gtttggttgt | gaataataga | acacccaaa | taacagtaac | ctcaacagaa | 6060 |
| aagaagtttg | tgcctccttc | acataaatga | tacacaggcg | gtcccaggca | gatccgtggg | 6120 |
| ccaggaccct | ggggtcctgc | tgttgctctg | tcccaccaag | tttgtcctca | agcttctgct | 6180 |
| ctcagaaggt | gacgtcctca | tgccaggcag | caagatggag | gaacagaggg | gaacagtatc | 6240 |
| cctcgggaaa | gctctagaag | tttctagaag | ctgcttgtga | cacctccatt | tacatccctt | 6300 |
| tggtcatatt | attgtcaaat | agccacacct | aactgcaaag | gaggctgaga | aatgcagggc | 6360 |
| atttgggggg | caatgggagg | cagggaaaca | gggaaacgtg | gacaattaat | tctatcacga | 6420 |
| gagaaggagg | gagagtaatt | tctggtgact | actagcagtc | tcatttacag | atgtgctgtg | 6480 |
| aatttctggg | acactgtgag | gtgggaggag | gtagcagggg | ctaaaggatt | gagtgtgttt | 6540 |
| ctatttcttt | ttttgttttt | tttttttttg | agatggagtc | tctcttggtc | acccagactg | 6600 |
| gagtgcagtg | gcgcaacttc | agctcactgc | aaactccgcc | tcccgggttc | aagcaattct | 6660 |
| cctgcctcag | cctcccgagt | agctgggatt | acaggtgccc | accaccacgt | ccggctaatt | 6720 |
| tttgtatttt | tagtagagac | agggtttcac | catcttggcc | aggctggtct | tgaactcctg | 6780 |
| acctcatgac | ccacccgcct | cggcctccca | aagtgctggg | attacaggcg | tgagccactg | 6840 |
| cgctcggcct | tgtgtttcta | tttcttcttg | tatctcgtgg | catgtctgct | tatgaagttg | 6900 |
| caattagagt | cttggagtag | agctattcat | aactgttagg | tcttcatgat | gagttccagt | 6960 |
| ctttagccct | ataatgcccc | ccttctttgc | ttttttcttt | aagatggcat | cttactctgt | 7020 |
| tgcccaggct | ggagtgcagt | ggtgcagcat | caacctccta | ggttcaagca | atcctcctgt | 7080 |
| ctcagcctcc | caagtagctg | ggattagagg | tgtgcaccac | cacacctggc | taattttttta | 7140 |
| attttttgta | gaggtgggct | cttgccatgt | tgcccaggct | ggtctcaaac | tcctgagctt | 7200 |
| aagcagtcct | cccaccttgg | cctcccaaag | cactgggatt | ataggcatga | gccaccaccc | 7260 |
| agccccttct | tgctttcat | ttaatggtta | ttgaactcat | atgtgagcag | tggtctattt | 7320 |

-continued

```
attccttcat tcaatactca ttttccaaat gcttgcattt gccaggtact ctgctagggg      7380
ctgggatcca gctaggagcg aggtacacaa gtcaccatcc cctggaagcc tccactcacg      7440
ttatgggcag ccagggatgg gttcaagtgg caaaggaaca ctggtcagaa tgtctctttc      7500
cttggcatca cctgctagat ctatgtctgt gcaggaggaa cagcacaagg ccatgggtct      7560
ttctttagga taaatgccca agaattccaa ggctcaggaa tgtctgaggt ctggcccttg      7620
gctctcaggc ccagtggcct gtttgcttcc tcactggatg gaagtcgggg gaggacaagc      7680
taggaagtgg gcagagtcta actgagaact cgcacatctc aggcaagggc tgtgtccgct      7740
gtgctttgtg atacctctgt gtaagcaact tgggtttgcc attcaggggg ttttccact      7800 gcatgtcccc aggaaggcca ccagacacgg ctgcgagtcc ccgctgccac gcccaggaag      7860
gagacccagt tgacggtacc tgtgtgcgtg attcctgcag cttccccgag gcagtttctg      7920
ggcaccccca ggcctcaggc agccgctcac ctggctgccc ccggtgccag gactcccatg      7980
aaaggaagag cccgggaagc ctaagccccc agccctgcc acagtgtaag cgccacctga      8040
agcaggtcca gctgctcttc tgtgaggatc acgatgagcc catctgcctc atctgcagtc      8100
tgagtcagga gcaccaaggc caccgggtgc gccccattga ggaggtcgcc ctggaacaca      8160
aggtaggcac tccctgcctg tgggctcttc tctgccaggc acttggacac actgggcctt      8220
acttcatttt cccaacaact ctgggttgtt ggtgcattaa ccagcattct tgggctggaa      8280
atggcaagaa cacaatataa accagtccag caaagagggg agctacaggt ttatgttgct      8340
cagagatcca gggggagctg gcttcaggta tggctgaatc cagaggctca gaggaagtgc      8400
ctctcagctc tgctgccttt ggcaattcag ccattcctcc ctcctctttc ctgagcaccc      8460
ctccccatgc cgctggcagc agcaccctca gccttgctac cagaaggaga tgttcccctc      8520
cagagttggc accagctaaa gatggcagga gccaaattca agcttttcaa caagtgctgt      8580
ttttccagaa gaaaattcag aagcagctgg agcatctgaa gaagctgaga aaatcagggg      8640
aggagcagcg atcctatggg gaggagaagg cagtgagctt tctggtaagg tcagaggtgg      8700
ctgatggccc atccgtccct gggaggaagg tgggaagagt gagcagggt ccccgagatt      8760 ctgctgtggt tcacagggca gcagggatgg ccacctcctc tcaggggaca gagggtaacc      8820
agcagccaag ggtaagctca tccctgtaga gggagaccac cccagcagg cagggtcac      8880 ctctgaggat cctgtcatgc tttctctatac tcaccagaag atggtagaga gcaacctatg      8940
ccggtgacta ctgcagaaag atgggattga ggaaagggga ggagaacgcc actttctttt      9000
tttgtgacgg agtctcgctc tgtcacccag gttgtagtgc agtggtgtga tcttggctca      9060
ctgcaacctc tgcctcccgg gttcaagcga ttctcctgcc tcagcctcct gagtagctgg      9120
gattataggt gagtgccacc atgcctggct aattttgtat gttttagtag agatggggtt      9180
tcaccatgtt ggtcaggctg ttctcgaact cctgaactcg tgatccgccc gccttggcct      9240
cccaaagtac tgggattaca gatgtgagcc actgcgcccg gccaagaaca cttttaactt      9300
cataatttac tctctgtttt tttgttttgt ttccaagatg gagtctcgct ctgtcaccca      9360
ggctggagta cagtggcacg atcttggctt gctccaacct ccacctccga ggttcaagca      9420
attctcctgc ctcagcctcc ttagtggctg gaattacagg cgcctgccac cgcgcctggc      9480 taattttgt attttagta gagacgggat ttcaccgtgt tggccaggct ggtctcaaac      9540
tcctgacctc aggtgatcca cctgcctcgg cctcccaaag tgctgggatt acaggtgtga      9600
gccatcgtgc ctgggctggt tttttgtttt ttagggtttt ttttttttt ttttttttga      9660
```

-continued

```
gatggaatct cactccgtcg tccaggctgg ggtgcagtgg tgcaatctcg gctcactgca    9720
aaccttcgcc tccccagttg aagcaattct cctgcctcag cctcccgagt tgctgggact    9780
gtaggcacat gccaccactc ctggctaatt tttgtatttt tagtaaagac agagtttccc    9840
catgttggcc aggctggtct cgaactcctg atctcaagtg atctgcccaa ctcagcctcc    9900
caaagtgctg ggattacaga catgagccaa tgcacccagc ccaaatttcc ccattttata    9960
agacaacatt tatattggat tagggaccca cccaatccca gtaggaccac atcttaacta   10020
attacatctg caagaactct tatctccaaa taagatcaca tgctgagtac tgggggttag   10080
ggcttcaacg tgtaaatttt ggaagggaca cagttaaacc ttaacaccag gtttaaggac   10140
attttcccag agctagcccc agccatgctc agtcttttct ggaaggttcc agacaatatc   10200
gcctcctgct ctggaatcta ggccttgaag aggcagcata agcccacctc ttatccacct   10260
ccaggaggtg ggcttctggg ggttcctgga catccacgtc cacccacagc acagacccccc  10320 ataccctccct gtcctctgct ccccagaaac aaactgaagc gctgaagcag cgggtgcaga   10380
ggaagctgga gcaggtgtac tacttcctgg agcagcaaga gcatttcttt gtggcctcac   10440
tggaggacgt gggccagatg gttgggcaga tcaggaaggc atatgacacc cgcgtatccc   10500
aggacatcgc cctgctcgat gcgctgattg gggaactgga ggccaaggag tgccagtcag   10560
aatgggaact tctgcaggtg ggtgtgcctg gcccggcttt tcttgggtcc cctgtgccta   10620
tcaggatgcc tcaggctccc agctctgcca tcagccgtgc tggaacaagt gggtgaagcc   10680
ctaaggccta ggataggact tggtcttggt gacccacagt gcctcttgtg cccagacccc   10740
tttgatgagg tctctcagga gcccagggtg gcctggtatc cagggatct ctgccatttc    10800 ccagaaggga tcagcagggc ttgagggccg ttccattgca ggcctcgcca cctgggatgc   10860
ctgaattccc gtggttagaa ttagacttga agaaggtgc tccacttcca ctgacaccct    10920
agggcaggga gccctggtaa gtgcagcggg gagctaaaag tccaggagcc cagaagtaga   10980
ggccaggagt cagcccagcc actaggagcc tggtaaccga cagtttcctt ctttttttctc  11040 ctaggacatt ggagacatct tgcacaggta cagcgaggtc ctgtggtgta ccctgggggtg   11100 tcttgcagaa agcatatggg ggagacagtc ccagaaggga cctgggaggg agatgttccc   11160
aaccccgggg tctgtgattc cagactcctc ctttttctg cagcttccca aagcctctct    11220
ggatttgata gggagaaggg catctggtca gcagggaggc tggccgggta tggagctgca   11280
gactgggaag ggtgaattca gcccatcctg ctgaaacaag atggaggctc cctaagaaac   11340
cttccgagtg cattgtgtcc cgtgcagttc atctgatgaa agctgccct tcaggcctac     11400 tggtggcctt gggaagcttg tttggagtgg agctgggcta agcccagcag gaaggggagg   11460
ggagggaagg gacaggaaga ggctaagcct taaaatcacc tgggagcttt acaaaatccc   11520
ggtgtccttt tgtgtctggc ttcttcactt agcataatgt cttcgggctt catccgtgtt   11580
gtaacgtgta tcagaattta ttttcttttt atggctgaat catagtccag tgtgtgttca   11640
tacattttgc ttatccattc atggatatcg ggacttcttc taacttttgg tttgtgaata   11700
atgttgctat gaacaagggt gtacaaatat ctgcttgaga ccctgctttg ttattttggg   11760
tacctaccca gaagtggaac tgcgggacca tgtggttatc ctgtgtttaa ttttttttga   11820
ggaaccacca tcctaattct cacagggct gcatcgcttc acattccac cagcagcaca     11880 cagggctcc agtttctcca catctttgcc atcacttatt ttcttctgtt tcactctctc    11940
tctctctctt ttttttgaa acagacgtct tgctctgtca tccaggctgg agtgcagtgg    12000
cgcgatcttg gctcactaca acctctgcct cccaggttca aggattctc ccacctcagc    12060
```

```
ctccctagta gctgggacta caggagcgtg ccaccatgcc cagctaattt ttttggtaga   12120
cagggtttca ccatattagc caggctggtc tcaaactcct gacctcaagt gatccaccca   12180
ccttggcctc ccaaagcgct gggattgcag gcgtgagcac cgtgcccagc catttctctt   12240
tccttccttc cctccctccc tcccttcctt cctttcttcc ttccttcctt tcttttcttc   12300
ttgagacaag gtctcactcc catcactaag gctggagagc agtggcacag tcacagctca   12360
ctgcaggctc agcttcctgg gctcgggtga ttctgagtag ctggcatcct gagtagctgg   12420
gactacaggc atgtgctacc acttccggct acttttttgt attttttaata gagacagggt   12480 ttcgccatgt tgcccaagct ggacttgaac tcctgggctc aagcgatccc actgccccgg   12540
cctcctgaag tgctaggatt acaggcatga gccaccatac ctggtctatt tttttctgtt   12600
gttgctgttt ttataatagc cattctaatg gatgtgaagg gatattttgt tgtgtgtgtt   12660 ttttttttcat ttattatctt tttatttcaa tagaaagaaa ggggtgtata atcaatttga   12720
catagataat tctagtagat aatatcaatg tcattttaag tccattctga aaactccttg   12780
tggttttgat atccatgtct ttaaagcacc ccagtacatg acagtctgtg gccaaagttg   12840
aggaccagca tttagacctc tgaatccagg gaagactttt ctttgtgtag ctcaggctgg   12900
gctaggtgtg ccttgtggag aatgtagttc atttccagct cacgggtact tgggccaccc   12960
cctcgctccg gccttctctg gtcaacagtc ttttgtctct agggctaaga cagtgcctgt   13020
scctgcaaag tggaccactc ctcaagagat aaaacaaaag atccaactcc tccaccagaa   13080
gtcagagttt gtggagaaga gcacaaagta cttctcaggt agatgggctt gggagaagat   13140
tgaaggtgca tgctcacttc ctccctaaga tccacatagc ccagagcccc tcacttccct   13200
cctcttcccc tggtcttgct gacctgcctt caacctctcc tccatctgtc cctggctgag   13260
ggacctaact ccagcttctc tctgctccct ttcccacatt ttagaaaccc tgcgttcaga   13320
aatggaaatg ttcaatggtg agtccagcgg taatggtgtg tgctggcctg gggttgttgc   13380
agtgttccct tgtgctgttg acttgagggg ccctatttag aagacaaaaa aaaaaaccaa   13440
acacctggag caaaggtagg agaaaggtca tggcaggccc cccaggctct gtgcgtgact   13500
cattgactga gttgactcat tagaccacag tccccaacat ggcctgggtt cctgggagga   13560
acgggattat acccaacata gcatgcaggg ccctaagcag ggggttcctt gtctttcctt   13620
gttgtcagga cagtgtaatt tagcccctct taatgctaat gctcaggaat ttttttcccta   13680 tctgattttt ctccgtagtt ccagagctga ttggcgctca ggcacatgct ggtaagtgcc   13740
cagatcaagg caagtggccc tggcctgctg gatccctgtg ctctccccta ccacgttcca   13800
gaagaactac cctgtccctg tttcctgcag gtggggagaa ccctgtaggg atgttgccca   13860
tggaccccta cctaggtatt caaattttct ttgcagttaa tgtgattctg gatgcagaaa   13920
ccgcttaccc caacctcatc ttctctgatg atctgaagag tgttagactt ggaaacaagt   13980
gggagaggct gcctgatggc ccgcaaagat ttgacagctg tatcattgtt ctgggctctc   14040
cgagtttcct ctctggccgc cgttactggg aggtggaggt tggagacaag acagcatgga   14100
tcctgggagc ctgcaagaca tccataagca ggaaagggaa catgactctg tcgccagaga   14160
atggctactg ggtggtgata atgatgaagg aaaatgagta ccaggcgtcc agcgttcccc   14220
cgacccgcct gctaataaag gagcctccca agcgtgtggg catcttcgtg gactacagag   14280
ttggaagcat ctccttttac aatgtgacag ccrgatccca catctataca ttcgccagct   14340
gctctttctc tgggccccctt caacctatct tcagccctgg gacacgtgat ggagggaaga   14400
```

-continued

```
acacagctcc tctgactatc tgtccagtgg gtggtcaggg gcctgactga atgcccaaca   14460
ctgcatctct cttcctgctt ctggccttgt atcttgcatt cacactcaat agtcacggaa   14520
tgccgactag gtgctagctg ctatgggaaa tgcmaaaata acaaaatagt tactgtgccc   14580
acggagccct acccgattat agcagaggta agttaggaac gaacatgtta gtcaatccgg   14640
gtgaagacat gtactgatga cacaccatgg atttcagagg aggaagtacg gagtcgttgc   14700
ataatccgcc cctggtgggt ggcactctca ggtgctcctg aacagaagat ttggccctca   14760
ttttccctca gaaccccacg gcaaggatat atgtcccctt gttctctctg cttctgtctt   14820
gaggatatgg gaagcctaga gaaacgcaag cagactggat tgggatagaa gtatttgtgt   14880
acctggatta atgaactatg atttttttttt tttttttttg agaccaaatc ttgctctgtg   14940
gcccaggctg gagtgcagtg gcacgatctc agctcactgc aacctccacc tcccaggttc   15000
aagcgattct cctgcctcag cctcctgagc agctggggat tacaggtgcg tgccaccaca   15060
ccaggctggt tttcttgtat ttttagtaga gacgggggtt tcaccatgtt agccaggctg   15120
gtctcgaact cctgacctca ggtgatccac ccgcctcagc ctcccaaagt gctgggatta   15180
caggcatgag ccactgtgcc cggcctatga ttcttttttt ttttttttttt tgagacaaag   15240 ttttgctctt gtcacccagg ctggagtgca gtggtgcaat cttggctcgc aacctccgcc   15300
tcccaggttc aagagattct cctgcctcag cctccgaagt agctgggatt acaggcgccc   15360
gccaccatgc ccggctaatt ttttgcattt ttagtagaca tgaggtttca tcatgttggc   15420
caggccggtc tcaaactcct gacctcaggt gatgcaccca cctcagcctc ccaaagtgca   15480
gggattacag gcatgagcca ccatgccggg ccatgattct taagagaatt gactgggcct   15540
catgaataaa aaattagaa aatctggtca tttgcatttg tcactcaatc actgtggaat   15600
cccatttccc gactgcattt ncaggaagtc agatgggact actgtcatgg aaaaacattt   15660
gggcatgtta tttccaagtg tcagattatt ctgtcttggt ttgtatggga aaatctgcgg   15720
gttgtggaat attaggttct acttcacaca catcccgtgc atttgtcctt catttaaaga   15780
gatgtaaagg ggccgggcat ggtgactcac atctgtaatc tcagcatttt gggaggcaaa   15840
ggcgggtgga tcgcctgagc ccagggattg agaccagctg ggcaatgtgg cgaaaacccg   15900
tctctacaaa aaatacaaaa attagccata gggatggggg tgggaggatg gcttgagcgc   15960
aggagatcga ggctgcagca gtgaactgag actgcactac ggcaatccag cctgggcaac   16020
agagtgagtc cctgtctcca aaagtggat gttaggagta caaaaatcaa atgaagatta   16080
gatccaaact cctatgccaa ctcctctgtc ttcactacta gagtgtagat tagactcaga   16140
tactccatgg ctatgatgag agcaggtaaa cttgctgggc tttcctccac gagttttatt   16200
ctataagagt aatccacatc ccaggacagt tcacatgacc tacggcttag ctgttccctg   16260
cggtgggtca tgtcttattc ccgattctcc cttgttataa gcttttcatg aatatctttg   16320
tgtatatttt ccaccacctc accatataca tattttttttc tcctgtgtta ttcctaaaat   16380
ggttcctgaa tgtgaaatat ctgataatgc ttcctacggg ttgccatacc atcctttgca   16440 aagatttta aaatatttca tgcccaaagc aatgactgcc atttaaaatt ttttttgctga   16500 tttaataggg atgtaatgag gccttacttc tgttttattt cattacctgt taatgaggct   16560
gtgaattttt ccatgtgaat ttctgctttt tgcttcattc tatggaaatt gtacagttcc   16620
tttgaatact tgctatttgg aatctacata ttgaatttcg tgttttgctg tacttcctca   16680
ttacatggtt ttaggctggg tgcggtgctc acgcctgaaa tcccaacatt tgggagccg    16740 gaggtgggca ggatcggttg gcaatcgagg gtttcgagac cgagcctggg cagacatggc   16800
```

```
gaaacctcgc cctctaccta gaaagataaa caaattagcg caggcaatgg tggtgagcac    16860
ctgtagtcct agctgataag gtctaggttg a                                   16891
```

<210> SEQ ID NO 2
<211> LENGTH: 3470
<212> TYPE: DNA
<213> ORGANISM: homo sapiens
<220> FEATURE:

<400> SEQUENCE: 2

```
atggctaaga cccctagtga ccatctgctg tccaccctgg aggagctggt gccctatgac      60
ttcgagaagt tcaagttcaa gctgcagaac accagtgtgc agaaggagca ctccaggatc     120
ccccggagcc agatccagag agccaggccg gtgaagatgg ccactctgct ggtcacctac     180 tatgggaag agtacgccgt gcagctcacc ctgcaggtcc tgcgggccat caaccagcgc     240
ctgctggccg aggagctcca caggcagcc attcaggaat attccacaca agaaaacggc     300
acagatgatt ccgcagcgtc cagctccctg ggggagaaca agcccaggag cctgaagact    360
ccagaccacc ccgaggggaa cgaggggaac ggccctcggc cgtacggggg cggagctgcc    420
agcctgcggt gcagccagcc cgaggccggg aggggctgt cgaggaagcc cctgagcaaa     480
cgcagagaga aggcctcgga gggcctggac gcgcaggca agcctcggac ccggagcccg     540
gccctgccgg gcgggagaag ccccggcccc tgcaggcgc tagaggggg ccaggccgag      600 gtccggctgc gcagaaacgc cagctccgcg gggaggctgc aggggctggc ggggggcgcc    660
ccggggcaga aggagtgcag gcccttcgaa gtgtacctgc cctcgggaaa gatgcgacct    720
agaagccttg aggtcaccat ttctacaggg gagaaggcgc ccgcaaatcc agaaattctc    780
ctgactctag aggaaaagac agctgcgaat ctggactcgg caacagaacc ccgggcaagg    840
cccactccga tggaggggc atctgcggac ctgaaggaag ccctggaaa tccagaacat     900 tcggtcaccg gaaggccacc agacacggct gcgagtcccc gctgccacgc caggaagga    960 gacccagttg acgtacctg tgtgcgtgat tcctgcagct cccccgaggc agtttctggg    1020 caccccagg cctcaggcag ccgctcacct ggctgccccc ggtgccagga ctcccatgaa    1080
aggaagagcc cggaagcct aagccccag cccctgccac agtgtaagcg ccacctgaag     1140
caggtccagc tgctcttctg tgaggatcac gatgagccca tctgcctcat ctgcagtctg    1200
agtcaggagc accaaggcca ccgggtgcgc cccattgagg aggtcgccct ggaacacaag    1260
aagaaaattc agaagcagct ggagcatctg aagaagctga gaaaatcagg ggaggagcag    1320
cgatcctatg gggaggagaa ggcagtgagc tttctgaaac aaactgaagc gctgaagcag    1380
cgggtgcaga ggaagctgga gcaggtgtac tacttcctgg aacagcagga gcatttcttt    1440
gtggcctcac tggaggacgt gggccagatg gttgggcaga tcaggaaggc atatgacacc    1500
cgcgtatccc aggacatcgc cctgctcgat gcgctgattg gggaactgga ggccaaggag    1560
tgccagtcag aatgggaact ctgcaggac attggagaca tcttgcacag gctaagaca    1620 gtgcctgtcc ctgaaaagtg gaccactcct caagagataa acaaaagat ccaactcctc    1680 caccagaagt cagagtttgt ggagaagagc acaaagtact tctcagaaac cctgcgttca    1740
gaaatggaaa tgttcaatgt tccagagctg attggcgctc aggcacatgc tgttaatgtg    1800
attctggatg cagaaccgc ttaccccaac ctcatcttct ctgatgatct gaagagtgtt    1860
agacttggaa caagtggga gaggctgcct gatggccgc aaagatttga cagctgtatc    1920
attgttctgg gctctccgag tttcctctct ggccgccgtt actgggaggt ggaggttgga    1980
```

-continued

```
gacaagacag catggatcct gggagcctgc aagacatcca taagcaggaa agggaacatg    2040
actctgtcgc cagagaatgg ctactgggtg gtgataatga tgaaggaaaa tgagtaccag    2100
gcgtccagcg ttcccccgac ccgcctgcta ataaaggagc ctcccaagcg tgtgggcatc    2160
ttcgtggact acagagttgg aagcatctcc ttttacaatg tgacagccag atcccacatc    2220
tatacattcg ccagctgctc tttctctggg ccccttcaac ctatcttcag ccctgggaca    2280
cgtgatggag ggaagaacac agctcctctg actatctgtc cagtgggtgg tcaggggcct    2340
gactgaatgc ccaacactgc atctctcttc ctgcttctgg ccttgtatct tgcattcaca    2400
ctcaatagtc acggaatgcc gactaggtgc tagctgctat gggaaatgca aaataacaa    2460 aatagttact gtgcccacgg agcctacccg attatagcag aggtaagtta ggaacgaaca    2520
tgttagtcaa tccgggtgaa gacatgtact gatgacacac catggatttc agaggaggaa    2580
gtacggagtc gttgcataat ccgccccctgg tgggtggcac tctcaggtgc tcctgaacag    2640
aagatttggc cctcattttc cctcagaacc ccacggcaag gatatatgtc cccttgttct    2700
ctctgcttct gtcttgagga tatgggaagc ctagagaaac gcaagcagac tggattggga    2760
tagaagtatt tgtgtacctg gattaatgaa ctatgatttt ttttttttt ttttgagacc    2820 aaatcttgct ctgtggccca ggctggagtg cagtggcacg atctcagctc actgcaacct    2880
ccacctccca ggttcaagcg attctcctgc ctcagcctcc tgagcagctg ggattacagg    2940
tgcgtgccac cacaccaggc tggttttctt gtatttttag tagagacggg ggtttcacca    3000
tgttagccag gctggtctcg aactcctgac ctcaggtgat ccacccgcct cagcctccca    3060
aagtgctggg attacaggca tgagccactg tgcccggcct atgattcttt tttttttttt    3120
tttttgagac aaagttttgc tcttgtcacc caggctggag tgcagtggtg caatcttggc    3180
tcactgcaac ctccgcctcc caggttcaag agattctcct gcctcagcct ccgaagtagc    3240
tgggattaca ggcgcccgcc accatgcccg gctaattttt tgcattttta gtagacatga    3300
ggtttcatca tgttggccag gccggtctca aactcctgac ctcaggtgat gcacccacct    3360
cagcctccca aagtgcaggg attacaggca tgagccacca tgcctggcca tgattcttaa    3420
gagaattgac tgggcctcat gaataaaaaa attagaaaat ctaaaaaaaa                3470
```

<210> SEQ ID NO 3
<211> LENGTH: 781
<212> TYPE: PRT
<213> ORGANISM: homo sapiens
<220> FEATURE:

<400> SEQUENCE: 3

```
Met Ala Lys Thr Pro Ser Asp His Leu Leu Ser Thr Leu Glu Glu Leu
 1               5                  10                  15

Val Pro Tyr Asp Phe Glu Lys Phe Lys Phe Lys Leu Gln Asn Thr Ser
                20                  25                  30

Val Gln Lys Glu His Ser Arg Ile Pro Arg Ser Gln Ile Gln Arg Ala
            35                  40                  45

Arg Pro Val Lys Met Ala Thr Leu Leu Val Thr Tyr Gly Glu Glu
        50                  55                  60

Tyr Ala Val Gln Leu Thr Leu Gln Val Leu Arg Ala Ile Asn Gln Arg
65                  70                  75                  80

Leu Leu Ala Glu Glu Leu His Arg Ala Ala Ile Gln Glu Tyr Ser Thr
                85                  90                  95

Gln Glu Asn Gly Thr Asp Asp Ser Ala Ala Ser Ser Ser Leu Gly Glu
```

```
                    100                 105                 110
Asn Lys Pro Arg Ser Leu Lys Thr Pro Asp His Pro Glu Gly Asn Glu
            115                 120                 125
Gly Asn Gly Pro Arg Pro Tyr Gly Gly Ala Ala Ser Leu Arg Cys
    130                 135                 140
Ser Gln Pro Glu Ala Gly Arg Gly Leu Ser Arg Lys Pro Leu Ser Lys
145                 150                 155                 160
Arg Arg Glu Lys Ala Ser Glu Gly Leu Asp Ala Gln Gly Lys Pro Arg
                165                 170                 175
Thr Arg Ser Pro Ala Leu Pro Gly Gly Arg Ser Pro Gly Pro Cys Arg
            180                 185                 190
Ala Leu Glu Gly Gly Gln Ala Glu Val Arg Leu Arg Arg Asn Ala Ser
                195                 200                 205
Ser Ala Gly Arg Leu Gln Gly Leu Ala Gly Ala Pro Gly Gln Lys
    210                 215                 220
Glu Cys Arg Pro Phe Glu Val Tyr Leu Pro Ser Gly Lys Met Arg Pro
225                 230                 235                 240
Arg Ser Leu Glu Val Thr Ile Ser Thr Gly Glu Lys Ala Pro Ala Asn
                245                 250                 255
Pro Glu Ile Leu Leu Thr Leu Glu Glu Lys Thr Ala Ala Asn Leu Asp
            260                 265                 270
Ser Ala Thr Glu Pro Arg Ala Arg Pro Thr Pro Asp Gly Gly Ala Ser
                275                 280                 285
Ala Asp Leu Lys Glu Gly Pro Gly Asn Pro Glu His Ser Val Thr Gly
            290                 295                 300
Arg Pro Pro Asp Thr Ala Ala Ser Pro Arg Cys His Ala Gln Glu Gly
305                 310                 315                 320
Asp Pro Val Asp Gly Thr Cys Val Arg Asp Ser Cys Ser Phe Pro Glu
                325                 330                 335
Ala Val Ser Gly His Pro Gln Ala Ser Gly Ser Arg Ser Pro Gly Cys
            340                 345                 350
Pro Arg Cys Gln Asp Ser His Glu Arg Lys Ser Pro Gly Ser Leu Ser
            355                 360                 365
Pro Gln Pro Leu Pro Gln Cys Lys Arg His Leu Lys Gln Val Gln Leu
    370                 375                 380
Leu Phe Cys Glu Asp His Asp Glu Pro Ile Cys Leu Ile Cys Ser Leu
385                 390                 395                 400
Ser Gln Glu His Gln Gly His Arg Val Arg Pro Ile Glu Glu Val Ala
                405                 410                 415
Leu Glu His Lys Lys Lys Ile Gln Lys Gln Leu Glu His Leu Lys Lys
            420                 425                 430
Leu Arg Lys Ser Gly Glu Glu Gln Arg Ser Tyr Gly Glu Glu Lys Ala
            435                 440                 445
Val Ser Phe Leu Lys Gln Thr Glu Ala Leu Lys Gln Arg Val Gln Arg
    450                 455                 460
Lys Leu Glu Gln Val Tyr Tyr Phe Leu Glu Gln Glu His Phe Phe
465                 470                 475                 480
Val Ala Ser Leu Glu Asp Val Gly Gln Met Val Gly Gln Ile Arg Lys
            485                 490                 495
Ala Tyr Asp Thr Arg Val Ser Gln Asp Ile Ala Leu Leu Asp Ala Leu
            500                 505                 510
Ile Gly Glu Leu Glu Ala Lys Glu Cys Gln Ser Glu Trp Glu Leu Leu
    515                 520                 525
```

-continued

```
Gln Asp Ile Gly Asp Ile Leu His Arg Ala Lys Thr Val Pro Val Pro
    530                 535                 540
Glu Lys Trp Thr Thr Pro Gln Glu Ile Lys Gln Lys Ile Gln Leu Leu
545                 550                 555                 560
His Gln Lys Ser Glu Phe Val Glu Lys Ser Thr Lys Tyr Phe Ser Glu
                565                 570                 575
Thr Leu Arg Ser Glu Met Glu Met Phe Asn Val Pro Glu Leu Ile Gly
            580                 585                 590
Ala Gln Ala His Ala Val Asn Val Ile Leu Asp Ala Glu Thr Ala Tyr
        595                 600                 605
Pro Asn Leu Ile Phe Ser Asp Asp Leu Lys Ser Val Arg Leu Gly Asn
    610                 615                 620
Lys Trp Glu Arg Leu Pro Asp Gly Pro Gln Arg Phe Asp Ser Cys Ile
625                 630                 635                 640
Ile Val Leu Gly Ser Pro Ser Phe Leu Ser Gly Arg Arg Tyr Trp Glu
                645                 650                 655
Val Glu Val Gly Asp Lys Thr Ala Trp Ile Leu Gly Ala Cys Lys Thr
            660                 665                 670
Ser Ile Ser Arg Lys Gly Asn Met Thr Leu Ser Pro Glu Asn Gly Tyr
        675                 680                 685
Trp Val Val Ile Met Met Lys Glu Asn Glu Tyr Gln Ala Ser Ser Val
    690                 695                 700
Pro Pro Thr Arg Leu Leu Ile Lys Glu Pro Pro Lys Arg Val Gly Ile
705                 710                 715                 720
Phe Val Asp Tyr Arg Val Gly Ser Ile Ser Phe Tyr Asn Val Thr Ala
                725                 730                 735
Arg Ser His Ile Tyr Thr Phe Ala Ser Cys Ser Phe Ser Gly Pro Leu
            740                 745                 750
Gln Pro Ile Phe Ser Pro Gly Thr Arg Asp Gly Gly Lys Asn Thr Ala
        755                 760                 765
Pro Leu Thr Ile Cys Pro Val Gly Gly Gln Gly Pro Asp
    770                 775                 780

<210> SEQ ID NO 4
<211> LENGTH: 543
<212> TYPE: DNA
<213> ORGANISM: homo sapiens
<220> FEATURE:

<400> SEQUENCE: 4
accctgcgtt cagaaatgga aatgttcaat gttccagagc tgattggcgc tcaggcacat      60
gctgttaatg tgattctgga tgcagaaacc gcttacccca acctcatctt ctctgatgat     120
ctgaagagtg ttagacttgg aaacaagtgg gagaggctgc ctgatggccc gcaaagattt     180
gacagctgta tcattgttct gggctctccg agtttcctct ctggccgccg ttactgggag     240
gtggaggttg gagacaagac agcatggatc ctgggagcct gcaagacatc cataagcagg     300
aaagggaaca tgactctgtc gccagagaat ggctactggg tggtgataat gatgaaggaa     360
aatgagtacc aggcgtccag cgttcccccg acccgcctgc taataaagga gcctcccaag     420
cgtgtgggca tcttcgtgga ctacagagtt ggaagcatct ccttttacaa tgtgacagcc     480
agatcccaca tctatacatt cgccagctgc tctttctctg gccccttca acctatcttc     540 agc                                                                  543
```

```
<210> SEQ ID NO 5
<211> LENGTH: 181
<212> TYPE: PRT
<213> ORGANISM: homo sapiens
<220> FEATURE:

<400> SEQUENCE: 5

Thr Leu Arg Ser Glu Met Glu Met Phe Asn Val Pro Glu Leu Ile Gly
  1               5                  10                  15

Ala Gln Ala His Ala Val Asn Val Ile Leu Asp Ala Glu Thr Ala Tyr
             20                  25                  30

Pro Asn Leu Ile Phe Ser Asp Leu Lys Ser Val Arg Leu Gly Asn
         35                  40                  45

Lys Trp Glu Arg Leu Pro Asp Gly Pro Gln Arg Phe Asp Ser Cys Ile
 50                  55                  60

Ile Val Leu Gly Ser Pro Ser Phe Leu Ser Gly Arg Arg Tyr Trp Glu
 65                  70                  75                  80

Val Glu Val Gly Asp Lys Thr Ala Trp Ile Leu Gly Ala Cys Lys Thr
                 85                  90                  95

Ser Ile Ser Arg Lys Gly Asn Met Thr Leu Ser Pro Glu Asn Gly Tyr
            100                 105                 110

Trp Val Val Ile Met Met Lys Glu Asn Glu Tyr Gln Ala Ser Ser Val
            115                 120                 125

Pro Pro Thr Arg Leu Leu Ile Lys Glu Pro Pro Lys Arg Val Gly Ile
            130                 135                 140

Phe Val Asp Tyr Arg Val Gly Ser Ile Ser Phe Tyr Asn Val Thr Ala
145                 150                 155                 160

Arg Ser His Ile Tyr Thr Phe Ala Ser Cys Ser Phe Ser Gly Pro Leu
                165                 170                 175

Gln Pro Ile Phe Ser
            180

<210> SEQ ID NO 6
<211> LENGTH: 20
<212> TYPE: DNA
<213> ORGANISM: homo sapiens
<220> FEATURE:

<400> SEQUENCE: 6
aacctgcctt ttcttgctca                                              20

<210> SEQ ID NO 7
<211> LENGTH: 20
<212> TYPE: DNA
<213> ORGANISM: homo sapiens
<220> FEATURE:

<400> SEQUENCE: 7
cactcagcac tggatgagga                                              20

<210> SEQ ID NO 8
<211> LENGTH: 26
<212> TYPE: DNA
<213> ORGANISM: homo sapiens
<220> FEATURE:

<400> SEQUENCE: 8
atcattttgc atctggttgt ccttcc                                       26

<210> SEQ ID NO 9
```

<211> LENGTH: 26
<212> TYPE: DNA
<213> ORGANISM: homo sapiens
<220> FEATURE:

<400> SEQUENCE: 9 tccctgtag aaatggtgac ctcaag                                          26

<210> SEQ ID NO 10
<211> LENGTH: 26
<212> TYPE: DNA
<213> ORGANISM: homo sapiens
<220> FEATURE:

<400> SEQUENCE: 10
ggccgggagg gggctgtcga ggaagc                                         26

<210> SEQ ID NO 11
<211> LENGTH: 26
<212> TYPE: DNA
<213> ORGANISM: homo sapiens
<220> FEATURE:

<400> SEQUENCE: 11
tcgtgcccgg ccagccattc tttctc                                         26

<210> SEQ ID NO 12
<211> LENGTH: 22
<212> TYPE: DNA
<213> ORGANISM: homo sapiens
<220> FEATURE:

<400> SEQUENCE: 12
tgagaactcg cacatctcag gc                                             22

<210> SEQ ID NO 13
<211> LENGTH: 22
<212> TYPE: DNA
<213> ORGANISM: homo sapiens
<220> FEATURE:

<400> SEQUENCE: 13
aaggcccagt gtgtccaagt gc                                             22

<210> SEQ ID NO 14
<211> LENGTH: 21
<212> TYPE: DNA
<213> ORGANISM: homo sapiens
<220> FEATURE:

<400> SEQUENCE: 14
ttggcaccag ctaaagatgg c                                              21

<210> SEQ ID NO 15
<211> LENGTH: 21
<212> TYPE: DNA
<213> ORGANISM: homo sapiens
<220> FEATURE:

<400> SEQUENCE: 15
tctccctcta cagggatgag c                                              21

<210> SEQ ID NO 16
<211> LENGTH: 22
<212> TYPE: DNA

```
<213> ORGANISM: homo sapiens
<220> FEATURE:

<400> SEQUENCE: 16
tatcgcctcc tgctctggaa tc                                           22

<210> SEQ ID NO 17
<211> LENGTH: 23
<212> TYPE: DNA
<213> ORGANISM: homo sapiens
<220> FEATURE:

<400> SEQUENCE: 17
cactgtgggt caccaagacc aag                                          23

<210> SEQ ID NO 18
<211> LENGTH: 21
<212> TYPE: DNA
<213> ORGANISM: homo sapiens
<220> FEATURE:

<400> SEQUENCE: 18
tccaggagcc cagaagtaga g                                            21

<210> SEQ ID NO 19
<211> LENGTH: 21
<212> TYPE: DNA
<213> ORGANISM: homo sapiens
<220> FEATURE:

<400> SEQUENCE: 19
ttctccctat caaatccaga g                                            21

<210> SEQ ID NO 20
<211> LENGTH: 21
<212> TYPE: DNA
<213> ORGANISM: homo sapiens
<220> FEATURE:

<400> SEQUENCE: 20
agaatgtagt tcatttccag c                                            21

<210> SEQ ID NO 21
<211> LENGTH: 20
<212> TYPE: DNA
<213> ORGANISM: homo sapiens
<220> FEATURE:

<400> SEQUENCE: 21
catttctgaa cgcagggttt                                              20

<210> SEQ ID NO 22
<211> LENGTH: 23
<212> TYPE: DNA
<213> ORGANISM: homo sapiens
<220> FEATURE:

<400> SEQUENCE: 22
acctaactcc agcttctctc tgc                                          23

<210> SEQ ID NO 23
<211> LENGTH: 21
<212> TYPE: DNA
<213> ORGANISM: homo sapiens
<220> FEATURE:
```

```
<400> SEQUENCE: 23
agttcttctg gaacgtggta g                                      21

<210> SEQ ID NO 24
<211> LENGTH: 21
<212> TYPE: DNA
<213> ORGANISM: homo sapiens
<220> FEATURE:

<400> SEQUENCE: 24
ccagaagaac taccctgtcc c                                      21

<210> SEQ ID NO 25
<211> LENGTH: 20
<212> TYPE: DNA
<213> ORGANISM: homo sapiens
<220> FEATURE:

<400> SEQUENCE: 25
agagcagctg gcgaatgtat                                        20

<210> SEQ ID NO 26
<211> LENGTH: 20
<212> TYPE: DNA
<213> ORGANISM: homo sapiens
<220> FEATURE:

<400> SEQUENCE: 26
gaggtggagg ttggagacaa                                        20

<210> SEQ ID NO 27
<211> LENGTH: 20
<212> TYPE: DNA
<213> ORGANISM: homo sapiens
<220> FEATURE:

<400> SEQUENCE: 27
tcctcctctg aaatccatgg                                        20

<210> SEQ ID NO 28
<211> LENGTH: 20
<212> TYPE: DNA
<213> ORGANISM: homo sapiens
<220> FEATURE:

<400> SEQUENCE: 28
aagctcactg ccttctcctc                                        20

<210> SEQ ID NO 29
<211> LENGTH: 20
<212> TYPE: DNA
<213> ORGANISM: homo sapiens
<220> FEATURE:

<400> SEQUENCE: 29
gaggagaagg cagtgagctt                                        20

<210> SEQ ID NO 30
<211> LENGTH: 20
<212> TYPE: DNA
<213> ORGANISM: homo sapiens
<220> FEATURE:

<400> SEQUENCE: 30
```

```
gacttggaaa caagtgggag                                              20

<210> SEQ ID NO 31
<211> LENGTH: 20
<212> TYPE: DNA
<213> ORGANISM: homo sapiens
<220> FEATURE:

<400> SEQUENCE: 31
ctcccacttg tttccaagtc                                              20

<210> SEQ ID NO 32
<211> LENGTH: 17
<212> TYPE: DNA
<213> ORGANISM: homo sapiens
<220> FEATURE:

<400> SEQUENCE: 32
gtaaaacgac ggccagt                                                 17

<210> SEQ ID NO 33
<211> LENGTH: 20
<212> TYPE: DNA
<213> ORGANISM: homo sapiens
<220> FEATURE:

<400> SEQUENCE: 33
caggaaacag ctatgaccat                                              20

<210> SEQ ID NO 34
<211> LENGTH: 18
<212> TYPE: DNA
<213> ORGANISM: homo sapiens
<220> FEATURE:

<400> SEQUENCE: 34
gttttcccag tcacgacg                                                18

<210> SEQ ID NO 35
<211> LENGTH: 184
<212> TYPE: PRT
<213> ORGANISM: Artificial Sequence
<220> FEATURE:
<223> OTHER INFORMATION: Description of Artificial Sequence:/ Note =
      Synthetic construct

<400> SEQUENCE: 35

Val Asn Val Ile Leu Asp Ala Glu Thr Ala Tyr Pro Asn Leu Ile Phe
  1               5                  10                  15

Ser Asp Asp Leu Lys Ser Val Arg Leu Gly Asn Lys Trp Glu Arg Leu
                 20                  25                  30

Pro Asp Gly Pro Gln Arg Phe Asp Ser Cys Ile Ile Val Leu Gly Ser
             35                  40                  45

Pro Ser Phe Leu Ser Gly Arg Arg Tyr Trp Glu Val Glu Val Gly Asp
         50                  55                  60

Lys Thr Ala Trp Ile Leu Gly Ala Cys Lys Thr Ser Ile Ser Arg Lys
 65                  70                  75                  80

Gly Asn Met Thr Leu Ser Pro Glu Asn Gly Tyr Trp Val Val Ile Met
                 85                  90                  95

Met Lys Glu Asn Glu Tyr Gln Ala Ser Ser Val Pro Pro Thr Arg Leu
                100                 105                 110
```

Leu Ile Lys Glu Pro Pro Lys Arg Val Gly Ile Phe Val Asp Tyr Arg
            115                 120                 125

Val Gly Ser Ile Ser Phe Tyr Met Val Thr Ala Arg Ser His Ile Tyr
        130                 135                 140

Thr Phe Ala Ser Cys Ser Phe Ser Gly Pro Leu Gln Pro Ile Phe Ser
145                 150                 155                 160

Pro Gly Thr Arg Asp Gly Gly Lys Asn Thr Ala Pro Leu Thr Ile Cys
                165                 170                 175

Pro Val Gly Gly Gln Gly Pro Asp
            180

<210> SEQ ID NO 36
<211> LENGTH: 183
<212> TYPE: PRT
<213> ORGANISM: Artificial Sequence
<220> FEATURE:
<223> OTHER INFORMATION: Description of Artificial Sequence:/ Note =
      Synthetic construct

<400> SEQUENCE: 36

Val Asp Val Thr Leu Asp Pro Asp Thr Ala Tyr Pro Ser Leu Ile Leu
1               5                   10                  15

Ser Asp Asn Leu Arg Gln Val Arg Tyr Ser Tyr Leu Gln Gln Asp Leu
            20                  25                  30

Pro Asp Asn Pro Glu Arg Phe Asn Leu Phe Pro Cys Val Leu Gly Ser
        35                  40                  45

Pro Cys Phe Ile Ala Gly Arg His Tyr Trp Glu Val Glu Val Gly Asp
    50                  55                  60

Lys Ala Lys Trp Thr Ile Gly Val Cys Glu Asp Ser Val Cys Arg Lys
65                  70                  75                  80

Gly Gly Val Thr Ser Ala Pro Gln Asn Gly Phe Trp Ala Val Ser Leu
                85                  90                  95

Trp Tyr Gly Lys Glu Tyr Trp Ala Leu Thr Ser Pro Met Thr Ala Leu
            100                 105                 110

Pro Leu Arg Thr Pro Leu Gln Arg Val Gly Ile Phe Leu Asp Tyr Asp
        115                 120                 125

Ala Gly Glu Val Ser Phe Tyr Asn Val Thr Glu Arg Cys His Thr Phe
    130                 135                 140

Thr Phe Ser His Ala Thr Phe Cys Gly Pro Val Arg Pro Tyr Phe Ser
145                 150                 155                 160

Leu Ser Tyr Ser Gly Lys Ser Ala Ala Pro Leu Ile Ile Cys Pro
                165                 170                 175

Met Ser Gly Ile Asp Gly Phe
            180

<210> SEQ ID NO 37
<211> LENGTH: 178
<212> TYPE: PRT
<213> ORGANISM: Xenopus Laevis

<400> SEQUENCE: 37

Thr Pro Met Leu Leu Asp Pro Thr Ser Ala His Pro Asn Leu His Leu
1               5                   10                  15

Ser Asp Gly Leu Thr Ser Val Arg Tyr Gly Glu Asn Lys Leu Ser Leu
            20                  25                  30

Pro Asp Asn Pro Lys Ala Phe Ser Gln Cys Ile Leu Val Leu Gly Ser
        35                  40                  45

```
Gln Gly Phe Asp Ser Gly Arg His Tyr Trp Glu Val Glu Val Gly Asp
     50                  55                  60

Lys Thr Ala Trp Asp Val Gly Met Ala Ser Glu Ser Ser Asn Arg Lys
 65              70                  75                      80

Gly Lys Ile Lys Leu Asn Pro Lys Asn Gly Tyr Trp Ala Ile Trp Leu
                 85                  90                  95

Arg Asn Gly Asn Ala Tyr Lys Ala Leu Glu Ser Pro Ser Lys Ser Leu
            100                 105                 110

Ser Leu Ser Ser His Pro Arg Lys Ile Gly Val Tyr Val Asp Tyr Glu
            115                 120                 125

Gly Gly Gln Ile Ser Phe Tyr Asn Ala Asp Asp Met Thr Ile Ile Tyr
        130                 135                 140

Thr Phe Asn Ala Thr Phe Thr Glu Lys Leu Tyr Pro Tyr Leu Ser Pro
145                 150                 155                 160

Phe Leu His Asp Ser Gly Lys Asn Val Asp Pro Leu Arg Phe Val His
                165                 170                 175

Asn Lys
```

<210> SEQ ID NO 38
<211> LENGTH: 179
<212> TYPE: PRT
<213> ORGANISM: Pleurodeles Waltl

<400> SEQUENCE: 38

```
Ala Pro Leu Thr Leu Asp Pro Asn Thr Ala His Pro Asn Leu Val Leu
  1               5                  10                  15

Ser Glu Gly Leu Thr Ser Val Lys Tyr Thr Asp Thr Lys Gln Gln Leu
             20                  25                  30

Pro Asp Asn Pro Lys Arg Phe Ser Gln Cys Ile Leu Val Leu Gly Ala
             35                  40                  45

Glu Gly Phe Asp Ser Gly Lys His Tyr Trp Glu Val Glu Val Gly Asn
     50                  55                  60

Lys Thr Ala Trp Asp Val Gly Met Ala Ser Glu Ser Ser Asn Arg Lys
 65              70                  75                      80

Gly Lys Ile Lys Leu Asn Pro Lys Asn Gly Tyr Trp Ala Ile Trp Leu
                 85                  90                  95

Arg Asn Gly Asn Ala Phe Lys Ala Leu Glu Ser Pro Ser Lys Thr Leu
            100                 105                 110

Asn Leu Thr Ser Lys Pro Ser Lys Ile Gly Val Tyr Leu Asp Tyr Glu
            115                 120                 125

Gly Gly Gln Val Ser Phe Tyr Asn Ala Asp Asp Met Ser Pro Ile Tyr
        130                 135                 140

Thr Phe Asn Gly Ser Phe Thr Glu Lys Leu Tyr Pro Tyr Leu Ser Pro
145                 150                 155                 160

Phe Leu Gln Asp Ser Gly Lys Asn Ala Glu Pro Leu Lys Leu Val His
                165                 170                 175

Thr Lys Leu
```

<210> SEQ ID NO 39
<211> LENGTH: 185
<212> TYPE: PRT
<213> ORGANISM: Artificial Sequence
<220> FEATURE:
<223> OTHER INFORMATION: Description of Artificial Sequence:/ Note = Synthetic construct

<400> SEQUENCE: 39

```
Val His Ile Thr Leu Asp Pro Asp Thr Ala Asn Pro Trp Leu Ile Leu
  1               5                  10                  15

Ser Glu Asp Arg Arg Gln Val Arg Leu Gly Asp Thr Gln Gln Ser Ile
             20                  25                  30

Pro Gly Asn Glu Glu Arg Phe Asp Ser Tyr Pro Met Val Leu Gly Ala
             35                  40                  45

Gln His Phe His Ser Gly Lys His Tyr Trp Glu Val Asp Val Thr Gly
     50                  55                  60

Lys Glu Ala Trp Asp Leu Gly Val Cys Arg Asp Ser Val Arg Arg Lys
 65                  70                  75                  80

Gly His Phe Leu Leu Ser Ser Lys Ser Gly Phe Trp Thr Ile Trp Leu
             85                  90                  95

Trp Asn Lys Gln Lys Tyr Glu Ala Gly Thr Tyr Pro Gln Thr Pro Leu
            100                 105                 110

His Leu Gln Val Pro Pro Cys Gln Val Gly Ile Phe Leu Asp Tyr Glu
            115                 120                 125

Ala Gly Met Val Ser Phe Tyr Asn Ile Thr Asp His Gly Ser Leu Ile
        130                 135                 140

Tyr Ser Phe Ser Glu Cys Ala Phe Thr Gly Pro Leu Arg Pro Phe Phe
145                 150                 155                 160

Ser Pro Gly Phe Asn Asp Gly Gly Lys Asn Thr Ala Pro Leu Thr Leu
            165                 170                 175

Cys Pro Leu Asn Ile Gly Ser Gln Gly
            180                 185

<210> SEQ ID NO 40
<211> LENGTH: 197
<212> TYPE: PRT
<213> ORGANISM: Artificial Sequence
<220> FEATURE:
<223> OTHER INFORMATION: Description of Artificial Sequence:/ Note =
      Synthetic construct

<400> SEQUENCE: 40

Val Ser Val Thr Leu Asp Pro Gln Ser Ala Ser Gly Tyr Leu Gln Leu
  1               5                  10                  15

Ser Glu Asp Trp Lys Cys Val Thr Tyr Thr Ser Leu Tyr Lys Ser Ala
             20                  25                  30

Tyr Leu His Pro Gln Gln Phe Asp Cys Glu Pro Gly Val Leu Gly Ser
             35                  40                  45

Lys Gly Phe Thr Trp Gly Lys Val Tyr Trp Glu Val Glu Val Glu Arg
 50                  55                  60

Glu Gly Trp Ser Glu Asp Glu Glu Gly Asp Glu Glu Glu Gly
 65                  70                  75                  80

Glu Glu Glu Glu Glu Glu Glu Ala Gly Tyr Gly Asp Gly Tyr Asp
             85                  90                  95

Asp Trp Glu Thr Asp Glu Asp Glu Ser Leu Gly Asp Glu Glu Glu
            100                 105                 110

Glu Glu Glu Glu Glu Glu Glu Val Leu Glu Ser Cys Met Val Gly
            115                 120                 125

Val Ala Arg Asp Ser Val Lys Arg Lys Gly Asp Leu Ser Leu Arg Pro
        130                 135                 140

Glu Asp Gly Val Trp Ala Leu Arg Leu Ser Ser Ser Gly Ile Trp Ala
145                 150                 155                 160

Asn Thr Ser Pro Glu Ala Glu Leu Phe Pro Ala Leu Arg Pro Arg Arg
```

```
                165                 170                 175
Val Gly Ile Ala Leu Asp Tyr Glu Gly Gly Thr Val Thr Phe Thr Asn
            180                 185                 190

Ala Glu Ser Gln Glu
        195

<210> SEQ ID NO 41
<211> LENGTH: 174
<212> TYPE: PRT
<213> ORGANISM: Artificial Sequence
<220> FEATURE:
<223> OTHER INFORMATION: Description of Artificial Sequence:/ Note =
      Synthetic construct

<400> SEQUENCE: 41

Ala Asp Val Ile Leu Asp Pro Lys Thr Ala Asn Pro Ile Leu Leu Val
1               5                   10                  15

Ser Glu Asp Gln Arg Ser Val Gln Arg Ala Lys Glu Pro Gln Asp Leu
            20                  25                  30

Pro Asp Asn Pro Glu Arg Phe Asn Trp His Tyr Cys Val Leu Gly Cys
        35                  40                  45

Glu Ser Phe Ile Ser Gly Arg His Tyr Trp Glu Val Glu Val Gly Asp
    50                  55                  60

Arg Lys Glu Trp His Ile Gly Val Cys Ser Lys Asn Val Gln Arg Lys
65                  70                  75                  80

Gly Trp Val Lys Met Thr Pro Glu Asn Gly Phe Trp Thr Met Gly Leu
                85                  90                  95

Thr Asp Gly Asn Lys Tyr Arg Thr Leu Thr Glu Pro Arg Thr Asn Leu
            100                 105                 110

Lys Leu Pro Lys Pro Lys Lys Val Gly Val Phe Leu Asp Tyr Glu
        115                 120                 125

Thr Gly Asp Ile Ser Phe Tyr Asn Ala Val Asp Gly Ser His Ile His
    130                 135                 140

Thr Phe Leu Asp Val Ser Phe Ser Glu Ala Leu Tyr Pro Val Phe Arg
145                 150                 155                 160

Ile Leu Thr Leu Glu Pro Thr Ala Leu Ser Ile Cys Pro Ala
                165                 170

<210> SEQ ID NO 42
<211> LENGTH: 174
<212> TYPE: PRT
<213> ORGANISM: Artificial Sequence
<220> FEATURE:
<223> OTHER INFORMATION: Description of Artificial Sequence:/ Note =
      Synthetic construct

<400> SEQUENCE: 42

Ile Lys Val Ile Leu Asp Tyr Asn Thr Ala His Asn Lys Val Ala Leu
1               5                   10                  15

Ser Glu Cys Tyr Thr Val Ala Ser Val Ala Glu Met Pro Gln Asn Tyr
            20                  25                  30

Arg Pro His Pro Gln Arg Phe Thr Tyr Cys Ser Gln Val Leu Gly Leu
        35                  40                  45

His Cys Tyr Lys Lys Gly Ile His Tyr Trp Glu Val Glu Leu Gln Lys
    50                  55                  60

Asn Asn Phe Cys Gly Val Gly Ile Cys Tyr Gly Ser Met Asn Arg Gln
65                  70                  75                  80

Gly Pro Glu Ser Arg Leu Gly Arg Asn Ser Ala Ser Trp Cys Val Glu
```

```
                      85                  90                  95
Trp Phe Asn Thr Lys Ile Ser Ala Trp His Asn Asn Val Glu Lys Thr
                100                 105                 110

Leu Pro Ser Thr Lys Ala Thr Arg Val Gly Val Leu Leu Asn Cys Asp
            115                 120                 125

His Gly Phe Val Ile Phe Ala Val Ala Asp Lys Val His Leu Met
130                 135                 140

Tyr Lys Phe Arg Val Asp Phe Thr Glu Ala Leu Tyr Pro Ala Phe Trp
145                 150                 155                 160

Val Phe Ser Ala Gly Ala Thr Leu Ser Ile Cys Ser Pro Lys
                165                 170

<210> SEQ ID NO 43
<211> LENGTH: 164
<212> TYPE: PRT
<213> ORGANISM: Artificial Sequence
<220> FEATURE:
<223> OTHER INFORMATION: Description of Artificial Sequence:/ Note =
      Synthetic construct

<400> SEQUENCE: 43

His Ile Ser Leu Asp Pro Gln Thr Ser His Pro Lys Leu Leu Leu Ser
1               5                   10                  15

Lys Asp His Gln Arg Ala Gln Phe Ser Tyr Lys Trp Gln Asn Ser Pro
            20                  25                  30

Asp Asn Pro Gln Arg Phe Asp Arg Ala Thr Cys Val Leu Ala His Thr
        35                  40                  45

Gly Ile Thr Gly Gly Arg His Thr Trp Val Val Ser Ile Asp Leu Ala
    50                  55                  60

His Gly Ala Ser Cys Thr Val Gly Val Val Ser Glu Asp Val Gln Arg
65                  70                  75                  80

Lys Gly Glu Leu Arg Leu Arg Pro Glu Glu Gly Val Trp Ala Val Arg
                85                  90                  95

Leu Ala Trp Gly Phe Val Ser Ala Leu Gly Ser Phe Pro Thr Arg Leu
                100                 105                 110

Thr Leu Lys Glu Gln Pro Arg Gln Val Arg Val Ser Leu Asp Tyr Glu
            115                 120                 125

Val Gly Trp Val Thr Phe Thr Asn Ala Val Thr Arg Glu Pro Ile Tyr
        130                 135                 140

Thr Phe Thr Ala Ser Phe Thr Arg Lys Val Ile Pro Phe Phe Gly Leu
145                 150                 155                 160

Trp Gly Arg Gly

<210> SEQ ID NO 44
<211> LENGTH: 144
<212> TYPE: PRT
<213> ORGANISM: Porcine

<400> SEQUENCE: 44

Ala His Ile Ser Leu Asp Pro Gln Thr Ser His Pro Lys Leu Leu Leu
1               5                   10                  15

Ser Glu Asp Asn Gln Gln Ala Arg Phe Ser Tyr Lys Trp Gln Asn Ser
            20                  25                  30

Pro Asp Asn Pro Gln Arg Phe Asp Arg Ala Thr Cys Val Leu Ala His
        35                  40                  45

Ser Gly Phe Thr Glu Gly Arg His Thr Trp Val Val Ser Val Asp Leu
    50                  55                  60
```

Ala His Gly Gly Ser Cys Thr Val Gly Val Val Ser Gln Asp Ile Arg
65                  70                  75                  80

Arg Lys Gly Glu Leu Arg Met Arg Pro Glu Glu Gly Val Trp Ala Val
            85                  90                  95

Arg Leu Ala Trp Gly Phe Val Ser Ala Leu Gly Ser Phe Pro Thr Arg
            100                 105                 110

Leu Ala Leu Glu Glu His Pro Arg Gln Val Arg Val Ser Ile Asp Tyr
            115                 120                 125

Glu Val Gly Trp Val Thr Phe Val Asn Ala Val Thr Gln Glu Pro Ile
            130                 135                 140

<210> SEQ ID NO 45
<211> LENGTH: 146
<212> TYPE: PRT
<213> ORGANISM: Artificial Sequence
<220> FEATURE:
<223> OTHER INFORMATION: Description of Artificial Sequence:/ Note =
      Synthetic construct

<400> SEQUENCE: 45

Val Asp Val Met Leu Asn Pro Gly Ser Ala Thr Ser Asn Val Ala Ile
1               5                   10                  15

Ser Val Asp Gln Arg Gln Val Lys Thr Val Arg Thr Cys Thr Phe Lys
            20                  25                  30

Asn Ser Asn Pro Cys Asp Phe Ser Ala Phe Gly Val Phe Gly Cys Gln
            35                  40                  45

Tyr Phe Ser Ser Gly Lys Tyr Tyr Trp Glu Val Asp Val Ser Gly Lys
        50                  55                  60

Ile Ala Trp Ile Leu Gly Val His Ser Lys Ile Ser Ser Leu Asn Lys
65                  70                  75                  80

Arg Lys Ser Ser Gly Phe Ala Phe Asp Pro Ser Val Asn Tyr Ser Lys
            85                  90                  95

Val Tyr Ser Arg Tyr Arg Pro Gln Tyr Gly Tyr Trp Val Ile Gly Leu
            100                 105                 110

Gln Asn Thr Cys Glu Tyr Asn Ala Phe Glu Asp Ser Ser Ser Ser Asp
            115                 120                 125

Pro Lys Val Leu Thr Leu Phe Met Ala Val Leu Pro Val Val Leu Gly
            130                 135                 140

Phe Ser
145